(12) United States Patent
Tanase et al.

(10) Patent No.: US 7,387,979 B2
(45) Date of Patent: Jun. 17, 2008

(54) MAGNESIUM COMPOUND, SOLID CATALYST COMPONENT FOR OLEFIN POLYMERIZATION, CATALYST FOR OLEFIN POLYMERIZATION AND METHOD FOR PRODUCING POLYOLEFIN

(75) Inventors: Shojiro Tanase, Ichihara (JP); Takanori Sadashima, Ichihara (JP); Hideo Funabashi, Ichihara (JP); Masahiko KJuramoto, Ichihara (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/515,766

(22) PCT Filed: May 19, 2003

(86) PCT No.: PCT/JP03/06195

§ 371 (c)(1),
(2), (4) Date: Nov. 24, 2004

(87) PCT Pub. No.: WO03/099749

PCT Pub. Date: Dec. 4, 2003

(65) Prior Publication Data

US 2005/0227857 A1    Oct. 13, 2005

(30) Foreign Application Priority Data

| May 24, 2002 | (JP) | 2002-150279 |
| May 24, 2002 | (JP) | 2002-150280 |
| May 24, 2002 | (JP) | 2002-151091 |
| May 24, 2002 | (JP) | 2002-151092 |

(51) Int. Cl.
*B01J 31/00* (2006.01)
(52) U.S. Cl. .................. 502/102; 502/103; 502/115
(58) Field of Classification Search ............... 502/102, 502/103, 115
See application file for complete search history.

(56) References Cited

U.S. PATENT DOCUMENTS

| 5,194,531 A | * | 3/1993 | Toda et al. | 526/125.3 |
| 5,556,820 A | * | 9/1996 | Funabashi et al. | 502/111 |
| 5,677,256 A | * | 10/1997 | Ala-Huikku et al. | 502/115 |
| 6,096,844 A | * | 8/2000 | Fushimi et al. | 526/128 |
| 6,777,365 B2 | * | 8/2004 | Tanase et al. | 502/115 |
| 6,790,804 B2 | * | 9/2004 | Gray et al. | 502/103 |
| 6,800,580 B1 | * | 10/2004 | Yang et al. | 502/103 |
| 6,831,033 B2 | * | 12/2004 | Yang et al. | 502/118 |
| 6,916,759 B2 | * | 7/2005 | Yang et al. | 502/125 |
| 2004/0198589 A1 | * | 10/2004 | Tanase et al. | 502/103 |
| 2004/0198931 A1 | * | 10/2004 | Tanase et al. | 526/123.1 |

FOREIGN PATENT DOCUMENTS

| EP | 0 544 006 A1 | 6/1993 |
| EP | 1 108 730 A1 | 6/2001 |
| JP | 58-811 | 1/1983 |
| JP | 61-260086 | 11/1986 |
| JP | 63-280707 | 11/1988 |
| JP | 3-074341 | 3/1991 |
| JP | 4-130107 | 5/1992 |
| JP | 5-1112 | 1/1993 |
| JP | 8-073388 | 3/1996 |
| WO | WO 93/00371 | 1/1993 |

* cited by examiner

*Primary Examiner*—Karl E Group
(74) *Attorney, Agent, or Firm*—Steptoe & Johnson LLP

(57) ABSTRACT

A magnesium compound obtained by reacting metallic magnesium having a sphericity (S) of less than 4.00, the sphericity (S) being represented by the following formula (I), an alcohol, and a halogen and/or a halogen-containing compound containing halogen atoms in an amount of 0.0001 gram atom or more relative to one gram atom of the metallic magnesium, $$S=(L_1/L_2)^3 \qquad (I)$$

wherein $L_1$ represents the maximum diameter of projection views of metallic magnesium determined by photographing with a scanning electron microscope and thereafter an image processing, and $L_2$ represents a diameter of a circle having an area equal to the area of the projection view of metallic magnesium. A solid catalyst component is obtained from the magnesium compound and a titanium compound, and a catalyst for olefin polymerization is obtained using the solid catalyst component.

4 Claims, 4 Drawing Sheets

Fig. 3

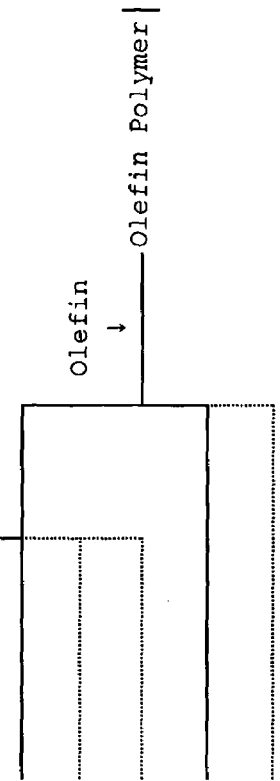

[A3] Solid Catalyst Component
  (a3) Mg Compound
    Metallic Mg Average Particle Size ($D_{50}$): 50 to 2,000 μm
    Alcohol Alcohol / Metallic Mg (ROH/Mg): 4 to 40 (Molar Ratio)
    Halogen and/or Halogen-containing Compound / Mg ≧ 0.0001
    Stirring Conditions ($n_3d_2$): $4.3\times10^3$ to $4.0\times10^6$
    (n: Number of Stirring, d: Diameter of Stirring Blade)
  (b3) Ti Compound
  (c3) Halogenated Compound
  (d3) Electron Donating Compound
[B] Organic Al Compound
[C] Electron Donating Compound → Olefin → Olefin Polymer

MAGNESIUM COMPOUND, SOLID CATALYST COMPONENT FOR OLEFIN POLYMERIZATION, CATALYST FOR OLEFIN POLYMERIZATION AND METHOD FOR PRODUCING POLYOLEFIN

TECHNICAL FIELD

The invention relates to a magnesium compound, a solid catalyst component for olefin polymerization, a catalyst for olefin polymerization and a method for producing a polyolefin.

TECHNICAL BACKGROUND

Hitherto, magnesium compounds such as magnesium chloride and magnesium alkoxides have been widely used as a support material without being milled in the field of catalysts for olefin polymerization, specifically the monopolymerization or copolymerization of olefins such as ethylene and propylene. This may improve the catalyst activity and the morphology of polyolefin powder.

For example, for improving an olefin polymer in the morphology including a particle size, form, etc., JP-A-S63-280707 discloses a method in which a magnesium compound is supported on an inorganic oxide such as silica, or JP-A-S58-000811 discloses a method in which a magnesium compound is once dissolved in a solvent such as an alcohol and then precipitate again, which precipitate is used.

However, these methods include very complicated steps, since they require the procedures of supporting, dissolving and precipitating a magnesium compound. Further, these methods have a defect that the catalyst is poor in stability of performance since the catalytic activity is high only at an early stage of the polymerization.

JP-A-H4-130107 discloses to use as a support of catalysts a magnesium compound obtained by reacting metallic magnesium, an alcohol and a certain amount of halogen. However, the sphericity or particle size distribution of support and polymer powder obtained may not be satisfactory dependently on the particulate properties of metallic magnesium or conditions under which a magnesium compound is produced.

In view of the foregoing the invention has been made and an object thereof is to provide a magnesium compound, a solid catalyst component for olefin polymerization, a catalyst for olefin polymerization and a method for producing a polyolefin, which can give a polyolefin with a narrow particle size distribution and/or a nearly spherical form without reducing stereoregularity and catalyst properties such as polymerization activity.

The inventors made efforts to find that the above subject can be solved by producing a solid catalyst component for olefin polymerization by reacting a magnesium compound and a titanium compound, the magnesium compound being obtained from metallic magnesium with a specified sphericity or particle size distribution index, or merallic magnesium with an oxidized coating film having a specified thickness; or obtained by reacting metallic magnesium with a specified average particle size, a specified amount of an alcohol and a halogen and/or a halogen-containing compound under specified stirring conditions. The invention has been completed by the finding.

DISCLOSURE OF THE INVENTION

The invention provides the following magnesium compound and the like.

[1] A magnesium compound obtained by reacting metallic magnesium having a sphericity (S) of less than 4.00, the sphericity (S) being represented by the following formula (I), an alcohol, and a halogen and/or a halogen-containing compound containing halogen atoms in an amount of 0.0001 gram atom or more relative to one gram atom of the metallic magnesium, $$S=(L_1/L_2)^3 \quad (I)$$

wherein $L_1$ represents the maximum diameter of projection views of metallic magnesium determined by photographing with a scanning electron microscope and thereafter an image processing, and $L_2$ represents a diameter of a circle having an area equal to the area of the projection view of metallic magnesium.

[2] A magnesium compound obtained by reacting metallic magnesium having a particle size distribution index (P) of less than 4.0, the index (P) being represented by the following formula (II), an alcohol, and a halogen and/or a halogen-containing compound containing halogen atoms in an amount of 0.0001 gram atom or more relative to one gram atom of the metallic magnesium, $$P=(D_{90}/D_{10}) \quad (II)$$

wherein $D_{90}$ represents a particle size of the metallic magnesium corresponding to 90% of cumulative weight percentage, and $D_{10}$ represents a particle size of the metallic magnesium corresponding to 10% of cumulative weight percentage.

[3] A magnesium compound obtained by reacting with stirring metallic magnesium, an average particle size ($D_{50}$) corresponding to 50% of cumulative weight percentage of the metallic magnesium being from 50 to 2,000 μm, an alcohol at a molar ratio relative to one mol of the metallic magnesium (ROH/Mg) of from 4 to 40, and a halogen and/or a halogen-containing compound containing halogen atoms in an amount of 0.0001 gram atom or more relative to one gram atom of the metallic magnesium, in a stirring vessel with a stirring axis provided with a stirring blade having a blade diameter d(m) at a speed of rotation n (number of revolution per minute) under conditions of $n^3d^2$ being from $4.3\times10^3$ to $4.0\times10^6$.

[4] A magnesium Compound Obtained by Reacting metallic magnesium having an oxidized coating film with a thickness of 1 μm or less, an alcohol, and a halogen and/or a halogen-containing compound containing halogen atoms in an amount of 0.0001 gram atom or more relative to one gram atom of the metallic magnesium.

[5] The magnesium compound according to any one of [1] to [4], wherein the halogen is iodine.

[6] The magnesium compound according to any one of [1] to [5], wherein the halogen-containing compound is magnesium chloride.

[7] The magnesium compound according to any one of [1] to [6], wherein the temperature of the reaction of the metallic magnesium, the alcohol and the halogen and/or the halogen-containing compound is from 30 to 90° C.

[8] The magnesium compound according to [1], which has a sphericity (S') of less than 1.30, the sphericity (S') being represented by the following formula (III), $$S'=(L_3/L_4)^3 \quad (III)$$

wherein $L_3$ represents the maximum diameter of projection views of the magnesium compound determined by photographing with a scanning electron microscope and thereafter an image processing, and $L_4$ represents a diameter of a circle having an area equal to the area of the projection view of magnesium compound.

[9] The magnesium compound according to [2] or [4], which has a particle size distribution index (P') of less than 3.4, the index (P') being represented by the following formula (IV), $$P'=(D_{90}/D_{10}) \quad (IV)$$

wherein $D_{90}$ represents a particle size of the magnesium compound corresponding to 90% of cumulative weight percentage, and $D_{10}$ represents a particle size of the magnesium compound corresponding to 10% of cumulative weight percentage.

[10] The magnesium compound according to [3], which has a particle size distribution index (P') of less than 3.4, the index (P') being represented by the formula (IV), and has a sphericity (S') of less than 1.30, the sphericity (S') being represented by the formula (III).

[11] The magnesium compound according to [4], which is metallic magnesium formed into particles in an atmosphere of an inert gas with an average diameter of 1 cm or less.

[12] A solid catalyst component for olefin polymerization, which is obtained by reacting
  (a) the magnesium compound according to any one of [1] to [11] and
  (b) a titanium compound.

[13] The solid catalyst component for olefin polymerization according to [12], which is obtained by reacting further (c) a halogenated compound and/or (d) an electron donating compound with the compounds (a) and (b).

[14] The solid catalyst component for olefin polymerization according to [13], wherein the hologenated compound (c) is silicon tetrachloride.

[15] A catalyst for olefin polymerization comprizing the following compounds [A] and [B], or the following compounds [A], [B] and [C]:
  [A] the solid catalyst component for olefin polymerization according to any one of [12] to [14];
  [B] an organic aluminum compound;
  [C] an electron donating compound.

[16] A method for producing a polyolefin using the catalyst for olefin polymerization according to [15].

[17] A method for producing a magnesium compound, comprising reacting
  metallic magnesium having a sphericity (S) of less than 4.00, the sphericity (S) being represented by the following formula (I),
  an alcohol, and
  a halogen and/or a halogen-containing compound containing halogen atoms in an amount of 0.0001 gram atom or more relative to one gram atom of the metallic magnesium, $$S=(L_1/L_2)^3 \quad (I)$$

wherein $L_1$ represents the maximum diameter of projection views of metallic magnesium determined by photographing with a scanning electron microscope and thereafter an image processing, and $L_2$ represents a diameter of a circle having an area equal to the area of the projection view of metallic magnesium.

[18] A method for producing a magnesium compound, comprising reacting
  metallic magnesium having a particle size distribution index (P) of less than 4.0, the index (P) being represented by the following formula (II),
  an alcohol, and
  a halogen and/or a halogen-containing compound containing halogen atoms in an amount of 0.0001 gram atom or more relative to one gram atom of the metallic magnesium, $$P=(D_{90}/D_{10}) \quad (II)$$

wherein $D_{90}$ represents a particle size of the metallic magnesium corresponding to 90% of cumulative weight percentage, and $D_{10}$ represents a particle size of the metallic magnesium corresponding to 10% of cumulative weight percentage.

[19] A method for producing a magnesium compound, comprising reacting with stirring
  metallic magnesium, an average particle size ($D_{50}$) corresponding to 50% of cumulative weight percentage of the metallic magnesium being from 50 to 2,000 μm,
  an alcohol at a molar ratio relative to one mol of the metallic magnesium (ROH/Mg) of from 4 to 40, and
  a halogen and/or a halogen-containing compound containing halogen atoms in an amount of 0.0001 gram atom or more relative to one gram atom of the metallic magnesium,
  in a stirring vessel with a stirring axis provided with a stirring blade having a blade diameter d(m) at a speed of rotation n (number of revolution per minute) under conditions of $n^3d^2$ being from $4.3 \times 10^3$ to $4.0 \times 10^6$.

[20] A method for producing a magnesium compound, comprising reacting
  metallic magnesium having an oxidized coating film with a thickness of 1 μm or less,
  an alcohol, and
  a halogen and/or a halogen-containing compound containing halogen atoms in an amount of 0.0001 gram atom or more relative to one gram atom of the metallic magnesium.

BRIEF DESCRIPTION OF DRAWINGS

FIG. 3 is a schematic drawing showing still another catalyst for olefin polymerization, and a process for producing an olefin polymer, provided by the invention.

PREFERRED EMBODIMENTS OF THE INVENTION

Figure 1:
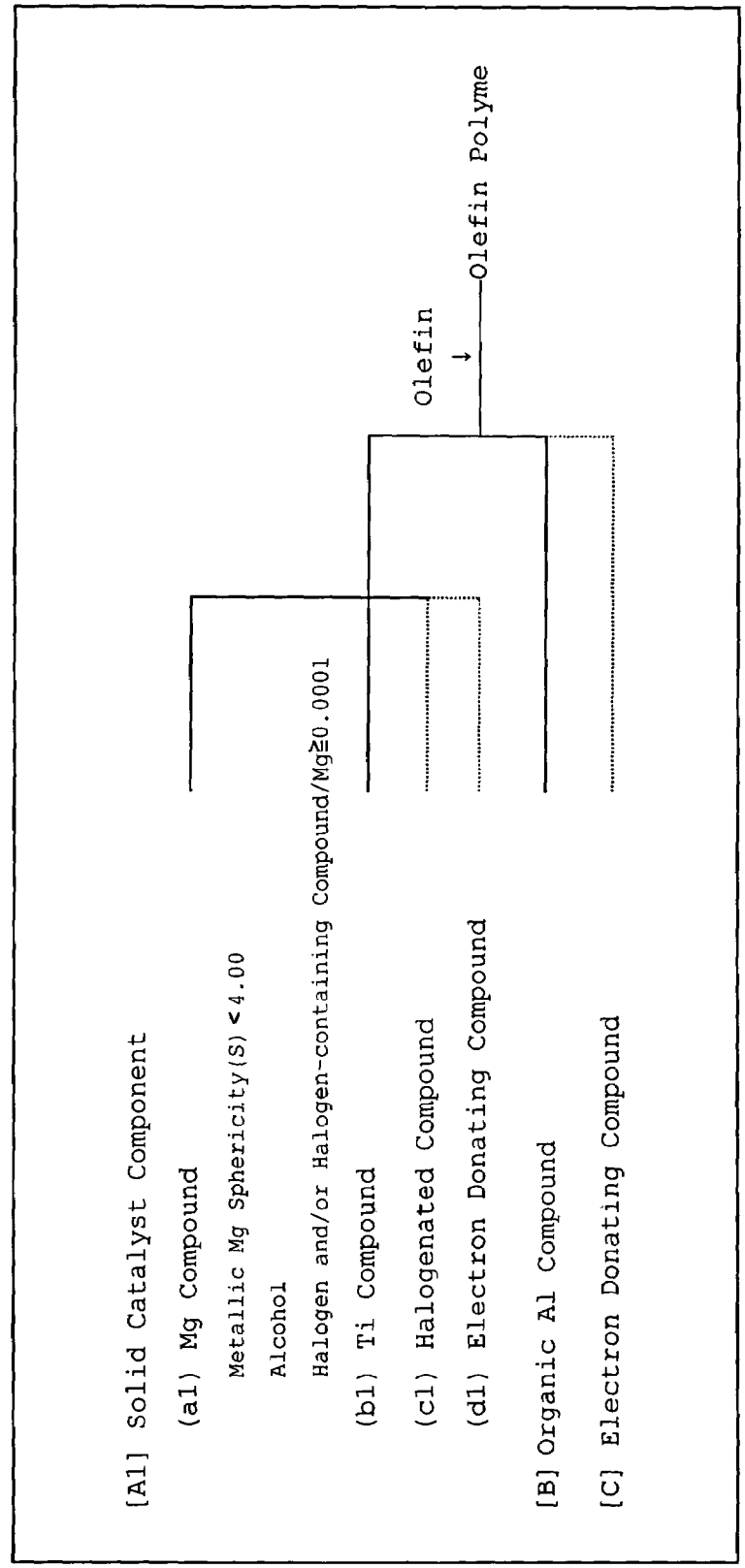
FIG. 1 is a schematic drawing showing the catalyst for olefin polymerization, and a process for producing an olefin polymer, provided by the invention.
Figure 2:
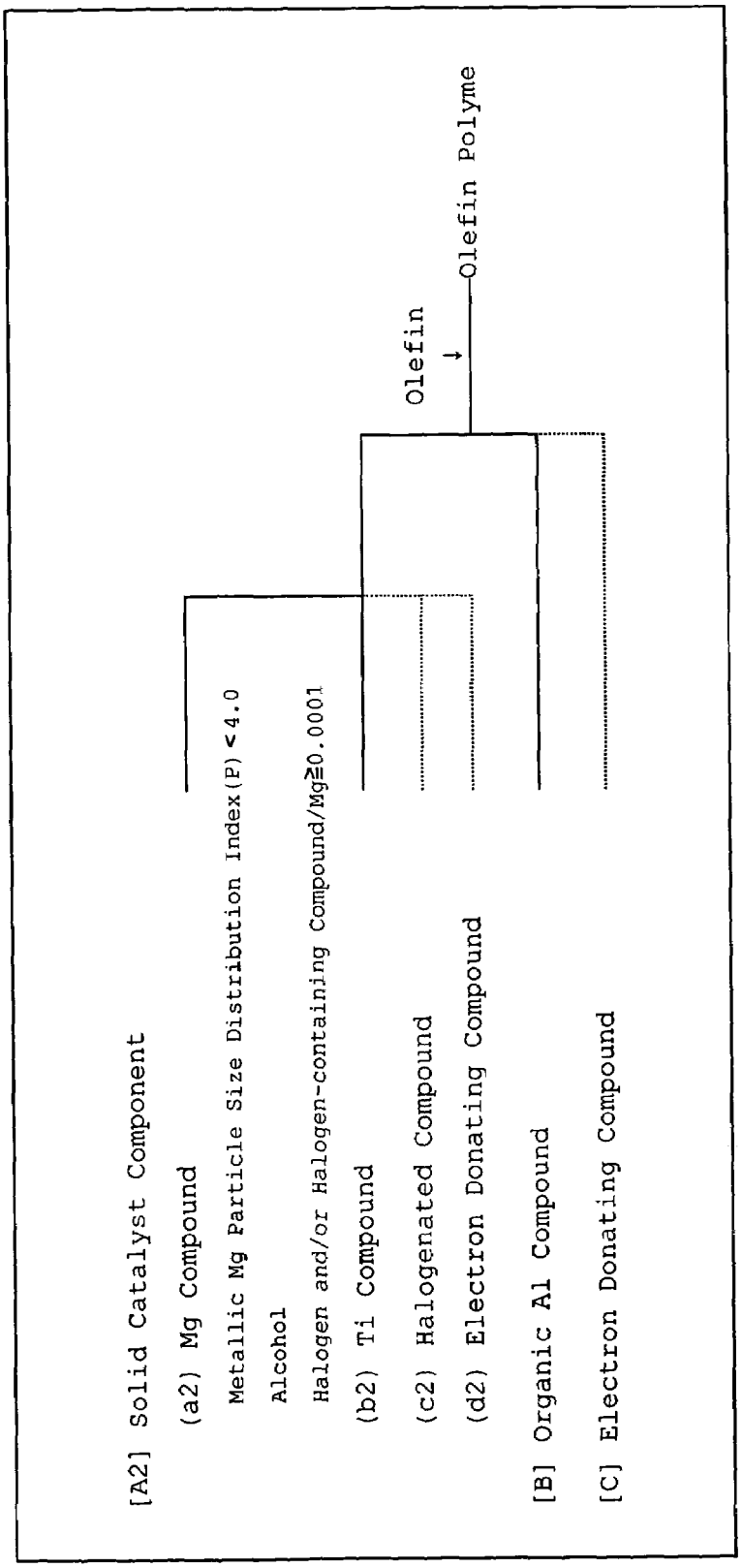
FIG. 2 is a schematic drawing showing another catalyst for olefin polymerization, and a process for producing an olefin polymer, provided by the invention.
Figure 4:
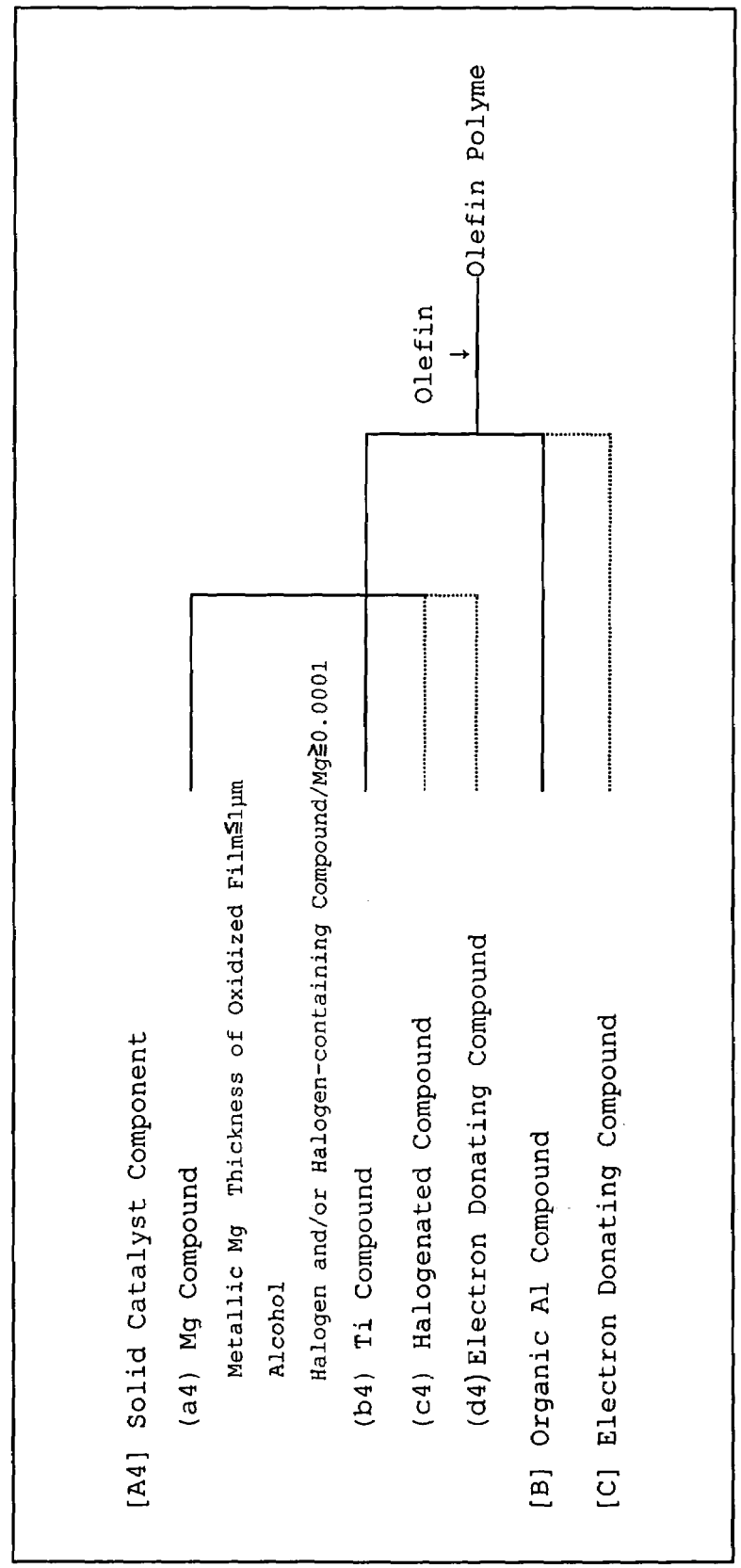
FIG. 4 is a schematic drawing showing yet another catalyst for olefin polymerization, and a process for producing an olefin polymer, provided by the invention.

Catalyst components and the like used in the invention will be explained hereinafter. The embodiments shown hereinafter are preferred embodiments, and the invention is not limited thereto.

1. Catalyst Components

[A1] Solid Catalyst Component for Olefin Polymerization (a1) Magnesium Compound

In view of the form of polymer particles and polymerization activity, the invention uses, as a magnesium compound (a1), a compound that is obtained by reacting metallic magnesium having a sphericity (S) of less than 4.00, preferably less than 2.50, an alcohol, and a halogen and/or a halogen-containing compound containing halogen atoms in an amount of 0.0001 gram atom or more relative to one gram atom of the metallic magnesium. The sphericity (S) is represented by the following formula (I), $$S=(L_1/L_2)^3 \qquad (I)$$

wherein $L_1$ represents the maximum diameter of projection views of metallic magnesium determined by photographing with a scanning electron microscope and thereafter an image processing, and $L_2$ represents a diameter of a circle having an area equal to the area of the projection view of metallic magnesium.

The form of polymer particles are degraded and polymerization activity also decrease, if the sphericity (S) of metallic magnesium is 4.00 or more. We think that this is caused by that the use of metallic magnesium with a low sphericity leads to the generation of large particles of solid catalyst component with a lower polymerization activity.

The sphericity (S) shows the degree of spherical form of a substance. The substance with sphericity=1 means a complete sphere. Metallic magnesium particles each are closer to a complete sphere as S is closer to 1.

Such metallic magnesium with a sphericity of less than 4.00 can be produced by the combination of cutting with a lathe, a file or the like and milling with a ball mill or the like, or an atomization method (melting/spray method).

The alcohol is preferably selected from lower alcohols having 1 to 6 carbon atoms. Ethanol is particularly preferred, since ethanol serves to give a solid product that remarkably improves the exhibition of catalytic performances of polymerization activity and the like. While the purity and water content of the alcohol are not critical, either. When an alcohol having a large water content is used, however, a coating film of magnesium hydroxide is formed on the metal magnesium surface, so that it is preferred to use an alcohol having a water content of 1% or less, and it is particularly preferred to use an alcohol having a water content of 2,000 ppm or less. Further, for obtaining an olefin polymer having better particle properties (individual particle shape and particle size distribution, hereinafter referred to as morphology in some cases), a smaller water content is preferred, and the water content is generally desirably 200 ppm or less.

The halogen is selected from chlorine, bromine or iodine, and iodine is particularly suitably used.

Further, the halogen atom of the halogen-containing compound is preferably chlorine, bromine or iodine. The halogen-containing compound is particularly preferably a halogen-containing metal compound. Specifically, the halogen-containing compound can be preferably selected from $MgCl_2$, $MgI_2$, $Mg(OEt)Cl$, $Mg(OEt)I$, $MgBr_2$, $CaCl_2$, $NaCl$ or $KBr$ etc. Of these, $MgCl_2$ is particularly preferred. The state, form and particle size of these compounds are not limited, and a compound being in any state and having any form and any particle size can be used. For example, a solution of such a compound in an alcohol solvent (e.g., ethanol) can be used.

It appears that Iodine or $MgCl_2$ is preferred, since the effect which improves the solubility of the magnesium compound to ethanol is high.

The amount of the alcohol per mole of the metal magnesium is preferably 2 to 100 mol, particularly preferably 5 to 50 mol. When the amount of the alcohol is too large, the yield of the magnesium compound (a1) having excellent morphology may decrease. When it is too small, stirring in a reaction vessel may not smoothly proceed, while the molar ratio is not limited thereto.

When the halogen or the halogen-containing compound is used, the amount of the halogen atoms in the halogen or the halogen-containing compound per gram atom of the metal magnesium is 0.0001 gram atom or more, preferably 0.0005 gram atom or more, more preferably 0.001 gram atom or more. When the amount of the halogen is less than 0.0001 gram atom, and when the magnesium compound (a1) is used as a support of a solid catalyst component, the catalyst may be poor in polymerization activity or an olefin polymer may be defective in morphology, and the like.

In the invention, the halogens and the halogen-containing compounds may be used solely each, and two or more halogens or halogen-containing compounds of these may be used in combination. Further, the halogen and the halogen-containing compound may be used in combination. When the halogen and the halogen-containing compound are used in combination, the amount of total halogen atoms in the halogen and the halogen-containing compound per gram atom of the metal magnesium is 0.0001 gram atom or more, preferably 0.0005 gram atom or more, more preferably 0.001 gram atom or more.

While the upper limit of the amount(s) of the halogen and/or the halogen-containing compound is not specially limited, the upper limit may be set as required so long as the magnesium compound (a1) for use in the invention can be obtained. Generally, the above upper limit is preferably less than 0.06 gram atom.

In the process for the production of the magnesium compound (a1), provided by the invention, the amount of the halogen and/or the halogen-containing compound is determined as required, whereby the particle size of the magnesium compound (a1) can be controlled as required.

The magnesium compound (a1) is usually prepared by reacting the metallic magnesium having the above sphericity (S), the alcohol and the halogen and/or the halogen-containing compound until the generation of hydrogen gas is no longer observed (generally, for 1 to 30 hours). Specifically, when iodine is used as a halogen, the magnesium compound (a1) can be prepared by a method in which iodine in the form of a solid is charged into the metal magnesium and the alcohol and then the mixture is allowed to react under heat, a method in which a solution of iodine in an alcohol is added dropwise to the metal magnesium and the alcohol and the mixture is allowed to react under heat, or a method in which, while the metal magnesium and an alcohol solution are heated, a solution of iodine in an alcohol is added dropwise to allow the mixture to react.

Each method is preferably carried out in the atmosphere of an inert gas (e.g., nitrogen gas or argon gas) and optionally in the presence of an inert organic solvent (e.g., saturated hydrocarbon such as n-hexane).

The metallic magnesium, the alcohol and the halogen and/or the halogen-containing compound are usually allowed to react at the temperature of 30 to 90° C., preferably at 30 to 60° C. The performance improves in the range thereof. It appears that the uniform magnesium compound can be produced since a balance between the rate of reaction and the solubility is excellent.

Further, it is not required to charge the entire amount of each of the metal magnesium, the alcohol and the halogen and/or the halogen-containing compound at once from the beginning, and they may be divided and partially charged. For example, the alcohol is entirely charged in the beginning, the metal magnesium is divided into several portions and such portions are charged separately. In this embodiment, the momentary generation of a large amount of hydrogen gas can be prevented, which is desirable in view of safety. Further, the size of a reaction vessel can be decreased. Further, it is also made possible to prevent the dissipation of alcohol, halogen and the like caused by the momentary generation of a large amount of hydrogen gas. While the number of the divisional portions can be determined by taking account of the size of the reaction vessel and is not specially limited, suitably, each is generally divided into five to ten portions in view of complicatedness of procedures.

Further, the reaction may be carried out by any one of a batch method and a continuous method. Furthermore, there may be employed a variant method in which the entire amount of the alcohol is charged in the beginning, a small amount of the metal magnesium is added to the alcohol, a product formed by a reaction is removed by separating it into other vessel, then, a small amount of the metal magnesium is charged, and these procedures are repeated.

When the magnesium compound (a1) thus obtained is used for the preparation of the solid catalyst component [A1], a dry product may be used, or a product obtained by filtering and then washing with an inert solvent such as heptane may be used.

In any case, the magnesium compound (a1) that is obtained in the invention can be used as a support of the solid catalyst component, without any pulverization or any sieving procedure for attaining a uniform particle size distribution. The magnesium compound (a1) is nearly spherical and has a sharp particle size distribution. Furthermore, the variation in sphericity of particles of the magnesium compound (a1) is small.

The magnesium compound (a1) generally has a sphericity (S') of less than 1.30, preferably less than 1.28. The sphericity (S') is represented by the following formula (III), $$S'=(L_3/L_4)^3 \quad \text{(III)}$$

wherein $L_3$ represents the maximum diameter of projection views of the magnesium compound determined by photographing with a scanning electron microscope and thereafter an image processing, and $L_4$ represents a diameter of a circle having an area equal to the area of the projection view of magnesium compound.

The magnesium compound (a1) with such a sphericity (S') is preferred in the view of catalyst activity and form of polymer particles.

Particles of magnesium compound (a1) each are closer to a complete sphere as S' is closer to 1, like the sphericity (S) of metallic magnesium.

The magnesium compound (a1) generally has a particle size distribution index (P') of less than 4.0, preferably less than 3.8. The index (P') is represented by the following formula (IV), $$P'=(D_{90}/D_{10}) \quad \text{(IV)}$$

wherein $D_{90}$ represents a particle size of the metallic magnesium (a1) corresponding to 90% of cumulative weight percentage, and $D_{10}$ represents a particle size of the metallic magnesium (a1) corresponding to 10% of cumulative weight percentage.

The use of the magnesium compound (a1) with such a particle size distribution index (P') enables to enhance polymerization activity and improve the form of polymer particles.

The particle size distribution index (P') shows the width of particle size distribution of magnesium compound (a1). A smaller value thereof means that the particle size distribution is narrow or sharp, or that many particles of magnesium compound (a1) with a uniform diameter are contained.

The magnesium compound (a1) with such a sphericity (S') of less than 1.30 and a particle size distribution index (P') of less than 4.0 can be produced by using metallic magnesium with the above-mentioned sphericity (S).

The magnesium compounds (a1) may be used solely, or two or more thereof may be used in combination.

Such magnesium compounds (a1) are solid, and substantially made of magnesium alkoxides practically.

Specific examples of the magnesium alkoxides include dialkoxymagnesium compounds such as dimethoxymagnesium, diethoxymagnesium, dipropoxymagnesium, dibutoxymagnesium, dihexyloxymagnesium, dioctoxymagnesium, diphenoxymagnesium and dicyclohexyloxymagnesium, diallyloxymagnesium; alkoxyalkylmagnesium compounds such as ethoxyethylmagnesium, phenoxymethylmagnesium, ethoxyphenylmagnesium, cyclohexyloxyphenylmagnesium, allyloxyalkylmagnesiu, alkoxyallylmagnesium, allyloxyallylmagnesium; alkoxymagnesium halides such as butoxymagnesium chloride, cyclohexyloxymagnesium chloride, phenoxymagnesium chloride, ethoxymagnesium chloride, ethoxymagnesium bromide, butoxymagnesium bromide and ethoxymagnesium iodide, and allyloxymagnesium halides. Of these alkoxy-group-containing magnesium compounds, dialkoxymagnesium compounds are preferred, and diethoxymagnesium is particularly preferred, in view of polymerization activity and stereoregularity.

(b1) Titanium Compound

In view of polymerization activity and the like, the titanium compound can be preferably selected from compounds represented by the following general formula (V), $$TiX_n(OR)_{4-n} \quad \text{(V)}$$

wherein X represents a halogen atom, and R is a hydrocarbon group having 1 to 10 carbon number. One of these may be the same as, or different from, the other or every other one. N is an integer of 0 to 4.

In the above general formula (V), the halogen atom X is preferably a chlorine or bromine atom, particularly preferably a chlorine atom. The hydrocarbon group R is preferably an alkyl group, an alkenyl group, a cycloalkenyl group, an aryl group or an aralkyl group and the like, and particularly preferably an linear or branched alkyl group. Further, R may be a saturated or an unsaturated group. It may be a linear or branched, or it may be cyclic, and it may contain a hetero element such as sulfur, nitrogen, oxygen, silicon or phosphorus. Specific examples of R include methyl, ethyl, n-propyl, isopropyl, n-butyl, sec-butyl, isobutyl, n-pentyl, n-hexyl, n-heptyl, n-octyl, n-decyl, allyl, butenyl, cyclopentyl, cyclohexyl, cyclohexenyl, phenyl, tolyl, benzyl and phenethyl and the like. And, n is perferably 4.

Specific examples of the titanium compounds (b1) of the above general formula (V) include tetraalkoxytitanium such as tetramethoxytitanium, tetraethoxytitanium, tetra-n-propoxytitanium, tetraisopropoxytitanium, tetra-n-butoxytitanium, tetraisobutoxytitanium, tetracyclohexyloxytitanium and tetraphenoxytitanium; titanium tetrahalides such as titanium tetrachloride, titanium tetrabromide and titanium tetraiodide; alkoxytitanium trihalides such as methoxytitanium trichloride, ethoxytitanium trichloride, propoxytitanium trichloride, n-butoxytitanium trichloride and ethoxytitanium tribromide; dialkoxytitanium dihalides such as dimethoxytitanium dichloride, diethoxytitanium dichloride, diisopropoxytitanium dichloride, di-n-propoxytitanium dichloride and diethoxytitanium dibromide; and trialkoxytitanium monohalides such as trimethoxytitanium chloride, triethoxytitanium chloride, triisopropoxytitanium chloride, tri-n-propoxytitanium chloride and tri-n-butoxytitanium chloride. Of these, high-halogenated titanium compounds are preferred, and titanium tetrachloride is particularly preferred, in view of polymerization activity. These titanium compounds (b1) may be used solely, or two or more thereof may be used in combination.

(c1) Halogenated Compound

If necessary, a halogenated compound (c1) is employed in a solid catalyst component for olefin polymerization. The halogenated compound (c1) is preferably used since it may improve the particulate form of an olefin polymer and make particle size distribution narrower. Halogenated compounds (c1) include halogens such as iodine, bromine, chlorine and fluorine; hydrogen halides such as hydrogen iodide, hydrogen bromide, hydrogen chloride and hydrogen fluoride; silicon tetrachloride and silicon tetrabromide; silicon halides such as trichlorosilane, dichlorosilane and monochlorosilane; carbon halides such as carbon tetrachloride and hexacholoroethane; halogen-substituted alcohols such as 2,2,2-trichloroethanol; halogen-substituted phenols such as p-chlorophenol; boron halides such as boron trichloride; aluminum halides such as aluminum trichloride; and tin halides such as tin tetrachloride. Of these, silicon tetrachloride is preferred in view of controlling the particle size of a polymer. These halogenated compounds (c1) may be used solely, or two or more thereof may be used in combination.

(d1) Electron-donating Compound

If necessary, an electron-donating compound (d1) is employed in a solid catalyst component for olefin polymerization. The electron-donating compound (d1) is preferably used since it may improve the stereoregularity of an olefin polymer. The electron-donating compounds (d1) include oxygen-containing compounds such as alcohols, phenols, ketones, aldehydes, carboxylic acids, malonic acid, esters of organic acids or inorganic acids and ethers such as monoether, diether and polyether, and nitrogen-containing compounds such as ammonia, amine, nitrile and isocyanate. Of these, esters of polyhydric carboxylic acids are preferred, and esters of aromatic polyhydric carboxylic acids are more preferred. Of these, a monoester and/or a diester of aromatic dicarboxylic acid are/is particularly preferred in view of polymerization activity. Further, the organic groups of the ester portions are preferably a linear, branched or cyclic aliphatic hydrocarbon group.

Specific examples of the electron-donating compounds include dialkyl esters such as methyl, ethyl, n-propyl, isopropyl, n-butyl, isobutyl, t-butyl, n-pentyl, 1-methylbutyl, 2-methylbutyl, 3-methylbutyl, 1,1-dimethylpropyl, 1-methylpentyl, 2-methylpentyl, 3-methylpentyl, 4-methylpentyl, 1-ethylbutyl, 2-ethylbutyl, n-hexyl, cyclohexyl, n-heptyl, n-octyl, n-nonyl, 2-methylhexyl, 3-methylhexyl, 4-methylhexyl, 2-ethylhexyl, 3-ethylhexyl, 4-ethylhexyl, 2-methylpentyl, 3-methylpentyl, 2-ethylpentyl or 3-ethylpentyl dicarboxylates such as phthalate, naphthalene-1,2-dicarboxylate, naphthalene-2,3-dicarboxylate, 5,6,7,8-tetrahydronaphthalene-1,2-dicarboxylate, 5,6,7,8-tetrahydronaphthalene-2,3-dicarboxylate, indan-4,5-dicarboxylate and indan-5,6-dicarboxylate. Of these, phthalic acid diesters are preferred, and phthalic acid diesters in which the organic group of an ester portion is a linear or branched aliphatic hydrocarbon group having 4 or more carbon atoms are particularly preferred. Preferable specific examples thereof include di-n-butyl phthalate, diisobutyl phthalate, di-n-heptyl phthalate and diethyl phthalate and the like. These electron-donating compounds (d1) may be used solely, or two or more thereof may be used in combination.

[A2] Solid Catalyst Component for Olefin Polymerization (a2) Magnesium Compound

In view of improving the form or morphology of polymer powder and polymerization activity, the invention uses, as a magnesium compound (a2), a compound that is obtained by reacting metallic magnesium having a particle size distribution index (P) of less than 4.0, preferably less than 3.0, an alcohol, and a halogen and/or a halogen-containing compound containing halogen atoms in an amount of 0.0001 gram atom or more relative to one gram atom of the metallic magnesium. The index (P) is represented by the following formula (II), $$P=(D_{90}/D_{10}) \qquad (II)$$

wherein $D_{90}$ represents a particle size of the metallic magnesium corresponding to 90% of cumulative weight percentage, and $D_{10}$ represents a particle size of the metallic magnesium corresponding to 10% of cumulative weight percentage.

The metallic magnesium with an index (P) of 4.0 or more is not preferred since a solid catalyst component with a high catalyst activity cannot be obtained from a magnesium compound prepared by reacting it.

Such metallic magnesium (a2) with a particle size distribution index of less than 4.0 can be produced by preparing particles by cutting, mechanically milling or melting/spray, and then sieving them with meshes and so on.

The metallic magnesium is not critical with regard to its form and the like so far as it has the above particle size distribution index. Therefore metallic magnesium having any particle form, for example, metallic magnesium having a granular, ribbon-shaped or powdery form, may be used.

The average particle size $D_{50}$ corresponding to 50% of cumulative weight percentage of the metallic magnesium is preferably 10 to 10,000 μm, more preferably 50 to 2,000 μm. If the average particle size is smaller, its reaction may proceed with violence and difficult to be controlled. If the particle size is too large, its reaction time may be long with a low producibility. If it is out of the range, the morphology such as particle size distribution and sphericity of a magnesium compound obtained may be degraded.

An alcohol, a halogen and a halogen-containing compound are the same as those explained in the magnesium compound (a1) and their explanation is thus omitted.

In order to produce the magnesium compound (a2), metallic magnesium with the above particle size distribution index (P), alcohol, and halogen and/or halogen-containing compound are generally reacted in the same manner as in the magnesium compound (a1).

The magnesium compound (a2) of the invention can be used as a support for a solid catalyst component without operations such as milling or classification for a narrow particle size distribution like the magnesium compound (a1). The magnesium compound (a2) is nearly spherical and has a sharp particle size distribution. The particles thereof have a small variability of sphericity.

The magnesium compound (a2) generally has a particle size distribution index (P') represented by the above formula (IV) of less than 3.4, preferably less than 3.2.

By using a magnesium compound (a2) with such a particle size distribution index (P'), the polymerization activity is enhanced and a polymer with more excellent particle morphology can be obtained.

The magnesium compound (a2) generally has a sphericity (S') represented by the above formula (III) of less than 2.00, preferably less than 1.50.

The magnesium compound (a2) with such a sphericity (S') is preferred in view of catalyst activity and morphology of polymer particles.

Such a magnesium compound (a2) with a particle size distribution index (P') of less than 3.4 and a sphericity (S') of less than 2.00 can be produced by using metallic magnesium with the above particle size distribution index (P).

The magnesium compound (a2) may be used solely or two or more thereof prepared by different methods may be used in combination.

Such a magnesium compound (a2) is solid and substantially made of a magnesium alkoxide. Examples of the magnesium alkoxide are the same as those of the magnesium compound (a1).

(b2) Titanium Compound

The titanium compound (b2) is as explained with regard to the titanium compound (b1) for use in the solid catalyst component [A1], so that its explanation is omitted.

(c2) Halogenated Compound

The halogenated compound (c2) is as explained with regard to the titanium compound (c1) for use in the solid catalyst component [A1], so that its explanation is omitted.

(d2) Electron-donating Compound

The electron-donating compound (d2) is as explained with regard to the electron-donating compound (d1) for use in the solid catalyst component [A1], so that its explanation is omitted.

[A3] Solid Catalyst Component for Olefin Polymerization (a3) Magnesium Compound

The invention uses, as a magnesium compound (a3), a compound that is obtained by reacting with stirring metallic magnesium, an average particle size ($D_{50}$) corresponding to 50% of cumulative weight percentage of the metallic magnesium being from 50 to 2,000 μm, an alcohol at a molar ratio relative to one mol of the metallic magnesium (ROH/Mg) of from 4 to 40, and a halogen and/or a halogen-containing compound containing halogen atoms in an amount of 0.0001 gram atom or more relative to one gram atom of the metallic magnesium, in a stirring vessel with a stirring axis provided with a stirring blade having a blade diameter d(m) at a speed of rotation n (number of revolution per minute) under conditions of $n^3d^2$ being from $4.3 \times 10^3$ to $4.0 \times 10^6$.

If $D_{50}$, ROH/Mg and $n^3d^2$ are out of the above range, the particle size distribution of polymer powder obtained may be wider, its sphericity may decrease or it may agglomerate.

We presume as to $D_{50}$ that the reason therefor is as follows. Particles of magnesium compound consist of plate-like crystals. The particle size and form of a magnesium compound depend on the balance of a reaction speed (promoting agglomeration of plate-like crystals), collision between particles, collision between particles and a wall of instrument or a shear from a fluid (suppressing agglomeration of crystals). From this point of view, if the reaction occurs at the same time, more uniform particles can be obtained. In the case of using particles with a smaller diameter, the reaction speed becomes higher due to the large specific surface area but the amount of a coating film becomes larger. This may influence the uniformity of reaction. We presume as to ROH/Mg that if the Mg concentration is too high, stirring may disadvantageously become ununiform, and if the Mg concentration is too low, particles may disadvantageously insufficiently collide with each other. We presume as to $n^3d^2$ that if the mixture is weakly stirred, its flow may become uniform with an ununiform reaction, and if it is strongly stirred, it may become difficult for the plate-like crystals of magnesium compound to agglomerate as larger particles.

$D_{50}$ is preferably 75 to 1,800 μm, ROH/Mg is preferably 5 to 20, and $n^3d^2$ is preferably $1.3 \times 10^4$ to $8.4 \times 10^5$.

Such metallic magnesium with an average particle size ($D_{50}$) of 50 to 2,000 μm can be produced by a mechanically milling, cutting, melting/spray and so on.

A blade diameter d and rotary speed n are not limited and they can be properly adjusted so far as $n^3d^2$ meets the above requirement.

Any blades used for slurry mixing stirring such as a max blend blade, full-zone blade, paddle (flat) blade, inclined blade, turbine blade and anchor blade may be used as the stirring blade. They may be used in ordinary form or multistage form. A plurality of baffles may be provided on the sidewall of a stirring vessel along the axial direction.

Of these blades, a max blend blade with baffles is preferred.

The metallic magnesium is not critical with regard to its form and the like so far as it has the above average particle size ($D_{50}$). Therefore metallic magnesium having any particle form, for example, metallic magnesium having a granular, ribbon-shaped or powdery form, may be used.

An alcohol, a halogen and a halogen-containing compound are the same as those explained in the magnesium compound (a1) except for the above-explanation and their explanation is thus omitted.

In order to produce the magnesium compound (a3), metallic magnesium with the above average particle size ($D_{50}$), alcohol with the above molar ratio (ROH/Mg), and halogen and/or halogen-containing compound with the above gram atomic ratio are reacted under the above stirring conditions like the magnesium compound (a1).

The magnesium compound (a3) of the invention can be used as a support for a solid catalyst component without operations such as milling or classification for a narrow particle distribution like the magnesium compound (a1). The magnesium compound (a3) is nearly spherical and has a sharp particle size distribution. The particles thereof have a small variability of sphericity.

The magnesium compound (a3) generally has a particle size distribution index (P') represented by the above formula (IV) of less than 3.4, preferably less than 3.2.

By using a magnesium compound (a3) with such a particle size distribution index (P'), the polymerization activity is enhanced and a polymer with more excellent particle morphology can be obtained.

The magnesium compound (a3) generally has a sphericity (S') represented by the above formula (III) of less than 1.30, preferably less than 1.28.

The magnesium compound (a3) with such a sphericity (S') is preferred in view of catalyst activity and morphology of polymer particles.

Such a magnesium compound (a3) with a particle size distribution index (P') of less than 3.4 and a sphericity (S') of less than 1.30 can be produced by reacting the above metallic magnesium, alcohol and halogen and/or halogen-containing compound under the above stirring conditions.

The magnesium compound (a3) may be used solely or two or more thereof prepared by different methods may be used in combination.

Such a magnesium compound (a3) is solid and substantially made of a magnesium alkoxide. Examples of the magnesium alkoxide are the same as those of the magnesium compound (a1).

(b3) Titanium Compound

The titanium compound (b3) is as explained with regard to the titanium compound (b1) for use in the solid catalyst component [A1], so that its explanation is omitted.

(c3) Halogenated Compound

The halogenated compound (c3) is as explained with regard to the titanium compound (c1) for use in the solid catalyst component [A1], so that its explanation is omitted.

(d3) Electron-donating Compound

The electron-donating compound (d3) is as explained with regard to the electron-donating compound (d1) for use in the solid catalyst component [A1], so that its explanation is omitted.

[A4] Solid Catalyst Component for Olefin Polymerization (a4) Magnesium Compound

In view of the form of polymer particles and polymerization activity, the invention uses, as a magnesium compound (a4), a compound that is obtained by reacting metallic magnesium having an oxidized coating film with a thickness of 1 μm or less, preferably 0.5 μm or less, more preferably 0.1 μm or less, an alcohol, and a halogen and/or a halogen-containing compound containing halogen atoms in an amount of 0.0001 gram atom or more relative to one gram atom of the metallic magnesium.

If metallic magnesium having an oxidized coating film with a thickness more than 1 μm is used, the particulate morphology of a magnesium compound (a4) or polyolefin obtained therefrom, or polymerization activity may be degraded.

Compounds constituting the oxidized coating film include $Mg(OH)_2$, $MgO$, $MgCO_3$, $MgSO_4$, double salts thereof and those containing crystal water. Examples of crystal-water-containing compounds include $MgSO_4 \cdot 7H_2O$. Examples of the double salts include $(MgCO_3)_4 \cdot Mg(OH)_2 \cdot 5H_2O$. The content thereof is generally 1 wt. % or less.

Such metallic magnesium having an oxidized coating film with a thickness of 1 μm or less can be produced by being formed into particles, for example, cutting, milling, sieving or melting/spray, in an atmosphere of an inert gas such as nitrogen.

The metallic magnesium is not critical with regard to its form and the like, so far as an oxidized coating film has a thickness of 1 μm or less. Therefore metallic magnesium having any particle form, for example, metallic magnesium having a granular, ribbon-shaped or powdery form, may be used. However, in order to ensure homogeneous reaction, particles with an average diameter of 1 cm or less are preferably used. When producing the particles with an average diameter of 1 cm or less, metallic magnesium may be subjected to processing such as cutting, milling, sieving and melting/spray preferably in an atmosphere of an inert gas such as nitrogen.

An alcohol, a halogen and a halogen-containing compound are the same as those explained in the magnesium compound (a1) and their explanation is thus omitted.

In order to produce the magnesium compound (a4), metallic magnesium satisfying the above requirements, an alcohol, a halogen and/or halogen-containing compound are reacted in the same manner as in the magnesium compound (a1).

The magnesium compound (a4) of the invention can be used as a support for a solid catalyst component without operations such as milling or classification for a narrow particle distribution like the magnesium compound (a1). The magnesium compound (a4) is nearly spherical and has a sharp particle size distribution. The particle thereof has a small variability of sphericity.

The magnesium compound (a4) generally has a particle size distribution index (P') represented by the above formula (IV) of less than 3.4, preferably less than 3.2.

The magnesium compound (a4) generally has a sphericity (S') represented by the above formula (III) of less than 2.00, preferably 1.50.

Such a magnesium compound (a4) with a particle size distribution index (P') of less than 3.4 and a sphericity (S') of less than 2.00 is preferred in view of catalyst activity and morphology of polymer particles. Using the above metallic magnesium can produce such a magnesium compound (a4).

The magnesium compound (a4) may be used solely or two or more thereof prepared by different methods may be used in combination.

Such a magnesium compound (a4) is solid and substantially made of a magnesium alkoxide. Examples of the magnesium alkoxide are the same as those of the magnesium compound (a1).

(b4) Titanium Compound

The titanium compound (b4) is as explained with regard to the titanium compound (b1) for use in the solid catalyst component [A1], so that its explanation is omitted.

(c4) Hologenated Compound

The hologenated compound (c4) is as explained with regard to the titanium compound (c1) for use in the solid catalyst component [A1], so that its explanation is omitted.

(d4) Electron-donating Compound

The electron-donating compound (d4) is as explained with regard to the electron-donating compound (d1) for use in the solid catalyst component [A1], so that its explanation is omitted.

[B] Organic Aluminum Compound

Although not specially limited, the organic aluminum compound [B] can be preferably selected from an organic aluminum compound having an alkyl group, a halogen atom, a hydrogen atom and an alkoxy group, aluminoxane, or a mixture of these. Specific examples thereof include trialkylaluminum compounds such as trimethylaluminum, triethylaluminum, triisopropylaluminum, triisobutylaluminum and trioctylaluminum; dialkylaluminum monochlorides such as diethylaluminum monochloride, diisopropylaluminum monochloride, diisobutylaluminum monochloride and dioctylaluminum monochloride; alkylaluminum sesquihalides such as ethylaluminum sesquichloride; and linear aluminoxanes such as methylaluminoxane. Of these organic aluminum compounds, trialkylaluminum having a lower alkyl group having 1 to 5 carbon atoms is preferred, and trimethylaluminum, triethylaluminum, tripropylaluminum and triisobutylaluminum are particularly preferred. These organic aluminum compounds [B] may be used solely, or two or more thereof may be used in combination.

[C] Electron-donating Compound

If necessary, an electron-donating compound [C] is used for a catalyst for olefin polymerization. The electron-donating compound [C] is preferably used since it may improve the stereoregularity of olefin polymer. The electron-donating compound [C] can be selected from an organosilicon compound having an alkoxy group, a nitrogen-containing compound, a phosphorus-containing compound or an oxygen-containing compound. Of these, it is particularly preferred to use an organosilicon compound having an alkoxy group.

Specific examples of the organosilicon compound having an alkoxy group include trimethylmethoxysilane, trimethylethoxysilane, triethylmethoxysilane, triethylethoxysilane, dimethyldimethoxysilane, dimethyldiethoxysilane, ethylisopropyldimethoxysilane, propylisopropyldimethoxysilane, diisopropyldimethoxysilane, diisobutyldimethoxysilane, isopropylisobutyldimethoxysilane, di-t-butyldimethoxysilane, t-butylmethyldimethoxysilane, t-butylethyldimethoxysilane, t-butylpropyldimethoxysilane, t-butylisopropyldimethoxysilane, t-butylbutyldimethoxysilane, t-butylisobutyldimethoxysilane, t-butyl(s-butyl)dimethoxysilane, t-butylamyldimethoxysilane, t-butylhexyldimethoxysilane, t-butylheptyldimethoxysilane, t-butyloctyldimethoxysilane, t-butylnonyldimethoxysilane, t-butyldecyldimethoxysilane, t-butyl(3,3,3-trifluromethylpropyl)dimethoxysilane, cyclohexylmethyldimethoxysilane, cyclohexylethyldimethoxysilane, cyclohexylpropyldimethoxysilane, cyclohexylisobutyldimethoxysilane, dicyclohexyldimethoxysilane, cyclohexyl-t-butyldimethoxysilane, cyclopentylmethyldimethoxysilane, cyclopentylethyldimethoxysilane, cyclopentylpropyldimethoxysilane, cyclopentyl-t-butyldimethoxysilane, dicyclopentyldimethoxysilane, cyclopentylcyclohexyldimethoxysilane, bis(2-methylcyclopentyl)dimethoxysilane, bis(2,3-dimethylcyclopentyl)dimethoxysilane, α-naphthyl-1,1,2-trimethylpropyldimethoxysilane, n-tetradecanyl-1,1,2-trimethylpropyldimethoxysilane, 1,1,2-trimethylpropylmethyldimethoxysilane, 1,1,2-trimethylpropylethyldimethoxysilane, 1,1,2-trimethylpropylisopropyldimethoxysilane, 1,1,2-trimethylpropylcyclopentyldimethoxysilane, 1,1,2-trimethylpropylcyclohexyldimethoxysilane, 1,1,2-trimethylpropylmyristyldimethoxysilane, diphenyldimethoxysilane, diphenyldiethoxysilane, phenyltriethoxysilane, methyltrimethoxysilane, methyltriethoxysilane, ethyltrimethoxysilane, ethyltriethoxysilane, propyltrimethoxysilane, isopropyltrimethoxysilane, butyltrimethoxysilane, butyltriethoxysilane, isobutyltrimethoxysilane, t-butyltrimethoxysilane, s-butyltrimethoxysilane, amyltrimethoxysilane, isoamyltrimethoxysilane, cyclopentyltrimethoxysilane, cyclohexyl trimethoxysilane, norbornenetrimethoxysilane, indenyl trimethoxysilane, 2-methylcyclopentyl trimethoxysilane, ethyltriisopropoxysilane, methylcyclopentyl(t-butoxy)dimethoxysilane, isopropyl(t-butoxy)dimethoxysilane, t-butyl(t-butoxy) dimethoxysilane, (isobutoxy)dimethoxysilane, vinyltriethoxysilane, vinyltributoxysilane, chlorotriethoxysilane, γ-chloropropyltrimethoxysilane, γ-aminopropyltriethoxysilane, 1,1,2-trimethylpropyltrimethoxysilane, 1,1,2-trimethylpropylisopropoxydimethoxysilane, 1,1,2-trimethylpropyl (t-butoxy)dimethoxysilane, tetramethoxysilane, tetraethoxysilane, tetrabutoxysilane, tetraisobutoxysilane, ethyl silicate, butyl silicate, trimethylphenoxysilane, methyltriallyloxysilane, vinyltris(β-methoxyethoxy)silane, vinyltrisacetoxysilane and dimethyltetraethoxydisiloxane and the like. Of these, dicyclopentyldimethoxysilane, cyclohexylisobutyldimethoxysilane and cyclohexylmethyldimethoxysilane are preferred.

Further, the above organosilicon compound also includes a compound obtained by reacting a silicon compound having no Si—O—C bond with an organic compound having an O—C bond in advance or by reacting these compounds during the polymerization of an α-olefin. Specifically, a compound obtained by reacting silicon tetrachloride and an alcohol is included.

Specific examples of the nitrogen-containing compound include 2,6-substituted piperidines such as 2,6-diisopropylpiperidine, 2,6-diisopropyl-4-methylpiperidine and N-methyl-2,2,6,6-tetramethylpiperidine; 2,5-substituted azolidines such as 2,5-diisopropylazolidine and N-methyl-2,2,5,5-tetramethylazolidine; substituted methylenediamines such as N,N,N',N'-tetramethylmethylenediamine and N,N,N',N'-tetraethylmethylenediamine; and substituted imidazolidines such as 1,3-dibenzylimidazolidine and 1,3-dibenzyl-2-phenylimidazolidine.

Specific examples of the phosphorus-containing compound include phosphorous acid esters such as triethyl phosphite, tri-n-propyl phosphite, triisopropyl phosphite, tri-n-butyl phosphite, triisobutyl phosphite, diethyl-n-butyl phosphite and diethylphenyl phosphite.

Specific examples of the oxygen-containing compound include 2,5-substituted tetrahydrofurans such as 2,2,5,5-tetramethyltetrahydrofuran and 2,2,5,5-tetraethyltetrahydrofuran; and dimethoxymethane derivatives such as 1,1-dimethoxy-2,3,4,5-tetrachlorocyclopentadiene, 9,9-dimethoxyfluorene and diphenyldimethoxymethane.

These electron-donating compounds [C] may be used solely, or two or more thereof may be used in combination.

2. Method of Preparation of Solid Catalyst Component

As a method of preparing the solid catalyst component [A1] to [A4], there is exemplified a method in which the above magnesium compound (a1) to (a4) and the titanium compound (b1) to (b4), if necessary, and the halogenated compound (c1) to (c4) and/or the electron-donating compound (d1) to (d4) are brought into contact and react with each other, and preferably the reaction mixture is thereafter brought into contact and reacts with the titanium compound (b1) to (b4) again (at least once). When the titanium compound (b1) to (b4) is brought into contact twice or more, the titanium compound (b1) to (b4) can be sufficiently supported on the magnesium compound (a1) to (a4) as a support of catalyst. The order of other contacts is not critical.

Further, these components may be brought into contact in the presence of an inert solvent such as a hydrocarbon, or each component may be diluted with an inert solvent such as a hydrocarbon before they are brought into contact. Examples of the above inert solvent include aliphatic hydrocarbons such as n-pentane, isopentane, n-hexane, n-heptane, n-octane and isooctane, aromatic hydrocarbons such as benzene, toluene, and xylene, or mixtures thereof. Of these, an aliphatic hydrocarbon is preferred.

The amount of the titanium compound (b1) to (b4) per mole of magnesium of the magnesium compound (a1) to (a4) is generally 0.5 to 100 moles, preferably 1 to 50 moles. If the amount is less than 0.5 mole, the polymerization activity per titanium may decrease. On the other hand, if it exceeds 100 moles, the polymerization activity per solid catalyst component may decrease.

When the hologenated compound (c1) to (c4) is used, the amount thereof per mole of magnesium of the magnesium compound (a1) to (a4) is generally 0.005 to 100 moles. If the amount is less than 0.005 mole, the polymerization activity per titanium or the stereoregularity of polymer may decrease. On the other hand, if it exceeds 100 moles, the polymerization activity per solid catalyst component may decrease.

Further, when the electron-donating compound (d1) to (d4) is used, the amount thereof per mole of magnesium of the magnesium compound (a1) to (a4) is generally 0.01 to 10 mol, preferably 0.05 to 0.15 mol. If the amount is less than 0.01 mole, the stereoregularity of polymer may decrease. On the other hand, if it exceeds 10 moles, the polymerization activity per titanium may decrease.

These compounds are brought into contact generally in a temperature range of −20 to 200° C., preferably 20 to 150° C. Further, the contact time is generally 1 minute to 24 hours, preferably 10 minutes to 6 hours. When the contact reaction is carried out at the above temperature and/or for the above time, the polymerization activity can be high and an olefin polymer can be obtained in an excellent form. Differing depending upon a type of a solvent when it is used and a contact temperature, etc., the pressure for the contact is generally in the range of 0 to 5 MPa, preferably 0 to 1 MPa. During the contacting procedures, preferably, they are stirred in view of the uniformity and efficiency of the contact. These contact conditions are also applicable to the contact reaction that is carried out for the second time or more with regard to the titanium compound (b1) to (b4).

When a solvent is used in the contact procedure of the titanium compound (b1) to (b4), the amount of the solvent per mole of the titanium compound (b1) to (b4) is generally 5,000 milliliters or less, preferably 10 to 1,000 milliliters. When the ratio is outside the above range, the uniformity or efficiency of the contact may be degraded.

Further, a reaction product, which is from the first contact reaction of the compounds, is washed with an inert solvent, generally at a temperature of 90 to 150° C., preferably 120 to 140° C. When the washing temperature is outside the above range, the catalyst activity or the stereoregularity may not be improved. The inert solvent can be selected from the already explained aliphatic hydrocarbons and aromatic hydrocarbons.

Although not especially limited with regard to the washing temperature after the contact reaction which is carried out for the second time or more with the titanium compound (b1) to (b4), the washing is carried out with an inert solvent, generally at a temperature of 90 to 150° C., preferably 120 to 140° C., in view of stereoregularity.

Although not especially limited, the washing method is preferably selected from a decantation or filtering method. Although the amount of the inert solvent, the washing time period and the number of times of the washing are not critical, the washing is carried out generally with a solvent in an amount, per mole of the magnesium compound (a1) to (a4), of 100 to 100,000 milliliters, preferably 1,000 to 50,000 milliliters, generally for 1 minute to 24 hours, preferably 10 minutes to 6 hours. When the above ratio is outside the above range, the washing may be incomplete.

While the pressure in the above case differs depending upon the type of the solvent, the washing temperature, and the like, the pressure is generally in the range of 0 to 5 MPa, preferably 0 to 1 MPa. For the uniformity of the washing and the washing efficiency, it is preferred to stir the reaction mixture during the washing. The thus-obtained solid catalyst component [A1] to [A4] can be stored in a dry state or in an inert solvent such as a hydrocarbon.

3. Process for Producing Olefin Polymer

Although the amount of each component of the catalyst for olefin polymerization is not especially limited, provided by the invention, each of the solid catalyst components [A1] to [A4] is used in such an amount that the titanium atom amount per liter of a reaction volume is generally in the range of 0.00005 to 1 mmol.

The organic aluminum compound [B] is used in such an amount that the aluminum/titanium (atomic ratio) is generally in the range of 1 to 1,000, preferably 10 to 1,000. When the above atomic ratio is outside the above range, the catalyst activity is sometimes insufficient.

Further, the electron-donating compound [C] is used in such an amount that the [C]/[B] (molar ratio) is generally in the range of 0.001 to 5.0, preferably 0.01 to 2.0, more preferably 0.05 to 1.0. When the above molar ratio is outside the above range, the sufficient catalyst activity and the stereoregularity sometimes cannot be obtained. When a preliminary polymerization is carried out, however, the amount of the electron-donating compound [C] can be further decreased.

The olefin for use in the invention is preferably an—olefin of the following general formula (VI).

$$R^1-CH=CH_2 \qquad VI$$

In the above general formula (VI), $R^1$ is a hydrogen atom or a hydrocarbon group, and the hydrocarbon group may be saturated or unsaturated, may be linear or branched, or may be cyclic. Specific examples of the olefin include ethylene, propylene, 1-butene, 1-pentene, 1-hexene, 1-heptene, 1-octene, 1-decene, 3-methyl-1-pentene, 4-methyl-1-pentene, vinylcyclohexane, butadiene, isoprene, piperylene, and the like. These olefins may be used solely, or two or more olefins thereof may be used in combination. Of the above olefins, ethylene and propylene are particularly preferred.

In the polymerization of an olefin in the invention, the preliminary polymerization of an olefin may be carried out as required before the regular polymerization thereof in view of the polymerization activity and the stereoregularity and power form of an olefin polymer. In this case, the preliminary polymerization of an olefin is carried out in the presence of a catalyst that is a mixture of predetermined amounts of the solid catalyst component [A1] to [A4], the organic aluminum compound [B] and optionally the electron-donating compound [C] generally in the temperature range of 0 to 100° C. under a pressure of atmospheric pressure to approximately 5 MPa, and then the regular polymerization of the olefin is carried out in the presence of the catalyst and the preliminary polymerization product. The polymerization activity and the particle properties of a polymer can be improved by carrying out the preliminary polymerization.

Although the polymerization type of the regular polymerization is not especially limited, any one of solution polymerization, slurry polymerization, gaseous phase polymerization, bulk polymerization, etc., can be employed. Further, any one of a batch polymerization and a continuous polymerization can be employed, and there can be employed two-step polymerization or multi-step polymerization that is carried out under different conditions.

Although the reaction condition is not especially limited, the polymerization pressure therefor is generally selected from the range of atmospheric pressure to 8 MPa, preferably 0.2 to 5 MPa, and the polymerization temperature is generally selected from the range of 0 to 200° C., preferably 30 to 100° C., as required in view of polymerization activity. Although differing depending upon olefins and the polymerization temperature, the polymerization time period is generally 5 minutes to 20 hours, preferably approximately 10 minutes to 10 hours.

The molecular weight of an olefin polymer can be adjusted by adding a chain transfer agent, preferably, hydrogen. Further, an inert gas such as nitrogen may be present. For the catalyst components of the invention, the solid catalyst component [A1] to [A4], the organic aluminum compound [B] and the electron-donating compound [C] may be mixed in predetermined amounts, and immediately thereafter, followed by the introduction of an olefin for polymerization. Alternatively, the above mixture may be aged for approximately 0.2 to 3 hours after the contact, and then followed by the introduction of an olefin for polymerization. Further, the above catalyst component may be suspended in an inert solvent, an olefin, or the like and fed. In the invention, the post treatment after the polymerization can be carried out according to a conventional method. That is, in a gaseous phase polymerization method, a nitrogen current may be allowed to pass through particles of a polymer powder introduced out of a polymerizer after the polymerization, for removing an olefin contained therein. Further, a polymer may be pelletized with an extruder as required, and in this case, a small amount of water, an alcohol or the like may be added for deactivating the catalyst completely. In a bulk polymerization method, a polymer that is withdrawn from a polymerizer after the polymerization can be pelletized after a monomer is completely separated from the polymer.

EXAMPLES

The invention will be explained with reference to Example hereinafter, while the invention shall not be limited to the following Examples. The sphericity (S), particle size distribution index (P), average particle size ($D_{50}$) and thickness of oxidized coating film of metallic magnesium; the sphericity (S') and particle size distribution index (P') of magnesium compounds; the sphericity (S'') and particle size distribution index (P'') of polymer powders; and the stereoregularity [mmmm] of polymers were determined as follows.

(1) Sphericity (S) of metallic magnesium: Metallic magnesium was photographed 40 times with a optical imcroscope (OLYMPUS Co., Ltd., BHS-751P). The photograph was subjected to image processing with an image analyzer (Nexsus Co., Ltd.). In the processing, particles less than 20 pixels (1 pixel: 0.4 μm×10.4 μm) were removed and the about 300 remaining particles were analyzed. The maximum diameter $L_1$ of projection views of the particles, and the diameter $L_2$ of the circle having the same area as that of projection view with the diameter $L_1$ were determined. Then a sphericity was calculated using the above formula (I).

(2) Particle size distribution index (P) of metallic magnesium: A particle size distribution measured with sieves was plotted on a logarithmic-normal probability paper, and a 50% particle size was used as an average particle size ($D_{50}$). Further, a 90% particle size ($D_{90}$) and a 10% particle size ($D_{10}$) were determined and then a particle size distribution index was calculated using the above formula (II).

(3) Average particle size ($D_{50}$) of metallic magnesium: A particle size distribution measured with sieves was plotted on a logarithmic-normal probability paper, and a 50% particle size was used as an average particle size ($D_{50}$).

(4) Thickness of oxidized coating film of metallic magnesium: Analysis was carried out with an ESCA (Electron Spectroscopy for Chemical Analysis). Specifically metallic magnesium was subjected to Ar ion etching and a layer from the uppermost surface to the depth of 3 μm was analyzed. The existence of an oxidized coating film was confirmed by using standard reagents ($MgCO_3$, $Mg(OH)_2$, $MgSO_4$, MgO, $MgSO_4$ $7H_2O$ and $(MgCO_3)_4$ $Mg(OH)_2$ $5H_2O$).

(5) Sphericity (S') of magnesium compound: A magnesium compound was dried and then photographed 300 times (150 times in Examples 15 to 18) with a scanning electron microscope (JEOL Ltd., JSM-25SIII) at an accelerating voltage of 5 KV to obtain a negative. Next the negative was image-processed by a transmission method. In the image processing, particles less than 20 pixels (1 pixel: 0.695 μm×0.695 μm (1.389 μm×1.389 μm in Examples 15 to 18)) were removed and the about 2,000 remaining particles were analyzed with an image analyzer (Nexsus Co., Ltd.). The maximum diameter $L_3$ of projection views of the particles, and the diameter $L_4$ of the circle having the same area as that of projection view with the diameter $L_3$ were determined. Then a sphericity was calculated using the above formula (III).

(6) Particle size distribution index (P') of magnesium compound: The particle size of a magnesium compound was measured by a light transmission method while the magnesium compound was suspended in a hydrocarbon. The particle size distribution measured was plotted on a logarithmic-normal probability paper, and a 50% particle size was used as an average particle size ($D_{50}$). Further, a 90% particle size ($D_{90}$) and a 10% particle size ($D_{10}$) were determined and then the particle size distribution index was calculated using the above formula (IV).

(7) Sphericity (S'') of polymer powder: In Examples 1 to 4 and Comparative Examples 1 to 3, the sphericity (S'') was measured in the same manner as the sphericity (S') of a magnesium compound.

In Examples 5 to 14 and Comparative Examples 4 to 12, the sphericity (S'') was measured in the same manner as the sphericity (S') of a magnesium compound except that the following. The polyolefin powder was photographed 40 times with a optical imcroscope (OLYMPUS Co., Ltd., BHS-751P), and the photograph was subjected to image processing. In the processing, one pixel was 10.4 μm×10.4 μm and about 300 particles were analyzed.

In Examples 15 to 18 and Comparative Examples 13 to 15, the sphericity (S'') was measured in the same manner as the sphericity (S') of a magnesium compound except that polyolefin powder was image-analyzed by a direct reflection method and one pixel was 0.0813 mm×0.0813 mm in the image analysis processing.

(8) Particle size distribution index (P'') of polymer powder: The particle size distribution index (P'') was measured in the same manner as the particle size distribution index (P) of metallic magnesium.

(9) Stereoregularity of polymer [mmmm]: A polymer was dissolved in 1,2,4-trichlorobenzene, and the stereoregularity of the polymer was quantitatively determined on the basis of signals of methyl group measured with a $^{13}$C-NMR (JEOL Ltd., EX-400) at 130° C. by a proton complete decoupling method.

The isotactic pentad fraction [mmmm] means the isotactic fraction in pentad units of a polypropylene molecule chain determined on the basis of $^{13}$C-NMR spectrum, proposed by A. Zambelli, et al., in Macromolecules, vol. 6, page 925 (1973).

Further, a method of determining assignment of peaks of $^{13}$C-NMR spectrum was according to the assignment proposed by A. Zambelli, et al., in Macromolecules, vol. 8, page 687 (1975).

Example 1

(1) Preparation of Magnesium Compound

A three-necked flask with a stirrer, having an internal volume of 0.5 L, was subjected to replacement of an atmosphere therein with nitrogen gas. The flask was charged with 122 g of ethanol (2.64 gram atoms), 0.8 g of iodine (6.3 mg atoms) and 8 g of metallic magnesium (0.33 gram atoms) with a sphericity of 1.85, which had been produced by an atomization method. The mixture was reacted with stirring (350 rpm) at 78° C. until hydrogen was not generated from the system to give a magnesium compound (diethoxymagnesium). Table 1 shows the results.

(2) Preparation of Solid Catalyst Component

A three-necked flask with a stirrer, having an internal volume of 0.5 L, was subjected to replacement of an atmosphere therein with nitrogen gas, and then the flask was charged with 80 mL of dehydrated octane and 16 g of the magnesium compound (support) prepared in the above (1). The mixture was heated to 40° C. Thereto was added 2.4 mL (23 mmol) of silicon tetrachloride and stirred for 20 minutes, followed by adding 3.4 mL (13 mmol) of di-n-butyl phthalate. The resultant solution was heated to 80° C. and 77 mL (0.70 mol) of titanium tetrachloride was dropwise added using a dropping funnel. Then, the mixture was stirred at an internal temperature of 125° C. for 1 hour to carry out a titanation procedure. After sufficiently washing with dehydrated octane, 122 mL (1.11 mol) of titanium tetrachloride was added and the mixture was stirred at an internal temperature of 125° C. for 2 hours to carry out a second titanation procedure. Sufficient washing with dehydrated octane gave a solid catalyst component.

(3) Propylene Slurry Polymerization

An autoclave made of stainless steel with a stirrer, having an internal volume of 1 L, was fully dried and then subjected to replacement of an atmosphere therein with nitrogen. The autoclave was charged with 500 mL of dehydrated heptane. The autoclave was further charged with 2.0 mmol of triethylaluminum, 0.25 mmol of dicyclopentyldimethoxysilane and 0.0025 mmol, as Ti atom, of the solid catalyst component prepared in the above (2), and hydrogen was introduced up to 0.1 MPa. Then, while propylene was introduced, the autoclave was temperature-increased to 80° C. and pressure-increased to a total pressure of 0.8 MPa, followed by polymerization for 1 hour.

Then, the temperature and the pressure in the autoclave were decreased, and the reaction product was taken out and poured into 2 L of methanol to deactivate the catalyst. The product was separated by filtration and vacuum-dried to give a polypropylene. Table 1 shows the results.

Example 2

(1) Preparation of Magnesium Compound

A magnesium compound was obtained in the same manner as in Example 1(1) except that the amount of iodine was changed to 0.24 g (1.9 mg atoms), the reaction temperature was changed to 50° C. and the stirring speed was changed to 525 rpm. Table 1 shows the results.

(2) Preparation of Solid Catalyst Component

A solid catalyst component was obtained in the same manner as in Example 1(2) except that the magnesium compound prepared in the above (1) was used.

(3) Propylene Slurry Polymerization

Propylene was polymerized in the same manner as in Example 1(3) except that the solid catalyst component prepared in the above (2) was used. Table 1 shows the results.

Example 3

(1) Preparation of Magnesium Compound

A magnesium compound was obtained in the same manner as in Example 1(1) except that the iodine was replaced with 0.30 g of anhydrous magnesium chloride (6.3 mg atoms) in Example 1(1). Table 1 shows the results.

(2) Preparation of Solid Catalyst Component

A solid catalyst component was obtained in the same manner as in Example 1(2) except that the magnesium compound prepared in the above (1) was used.

(3) Propylene Slurry Polymerization

Propylene was polymerized in the same manner as in Example 1(3) except that the solid catalyst component prepared in the above (2) was used. Table 1 shows the results.

Example 4

(1) Preparation of Magnesium Compound

A magnesium compound was obtained in the same manner as in Example 1(1) except that metallic magnesium with a sphericity of 2.93 (prepared by a cutting and ball mill method) was used. Table 1 shows the results.

(2) Preparation of Solid Catalyst Component

A solid catalyst component was obtained in the same manner as in Example 1(2) except that the magnesium compound prepared in the above (1) was used.

(3) Propylene Slurry Polymerization

Propylene was polymerized in the same manner as in Example 1(3) except that the solid catalyst component prepared in the above (2) was used. Table 1 shows the results.

Comparative Example 1

(1) Preparation of Magnesium Compound

A magnesium compound was obtained in the same manner as in Example 1(1) except that metallic magnesium with a sphericity of 5.20 (prepared by a cutting method) was used. Table 1 shows the results.

(2) Preparation of Solid Catalyst Component

A solid catalyst component was obtained in the same manner as in Example 1(2) except that the magnesium compound prepared in the above (1) was used.

(3) Propylene Slurry Polymerization

Propylene was polymerized in the same manner as in Example 1(3) except that the solid catalyst component prepared in the above (2) was used. Table 1 shows the results.

Comparative Example 2

(1) Preparation of Magnesium Compound

A magnesium compound was obtained in the same manner as in Example 1(1) except that metallic magnesium with a sphericity of 5.80 (prepared by a cutting method) was used and the reaction temperature was changed to 60° C. Table 1 shows the results.

(2) Preparation of Solid Catalyst Component

A solid catalyst component was obtained in the same manner as in Example 1(2) except that the magnesium compound prepared in the above (1) was used.

(3) Propylene Slurry Polymerization

Propylene was polymerized in the same manner as in Example 1(3) except that the solid catalyst component prepared in the above (2) was used. Table 1 shows the results.

Comparative Example 3

(1) Preparation of Magnesium Compound

A magnesium compound was obtained in the same manner as in Example 3(1) except that metallic magnesium with a sphericity of 6.95 (prepared by a cutting method) was used. Table 1 shows the results.

(2) Preparation of Solid Catalyst Component

A solid catalyst component was obtained in the same manner as in Example 1(2) except that the magnesium compound prepared in the above (1) was used.

(3) Propylene Slurry Polymerization

Propylene was polymerized in the same manner as in Example 1(3) except that the solid catalyst component prepared in the above (2) was used. Table 1 shows the results.

(2) Preparation of Solid Catalyst Component

A three-necked flask with a stirrer, having an internal volume of 0.5 L, was subjected to replacement of an atmosphere therein with nitrogen gas, and then the flask was charged with 80 mL of dehydrated octane and 16 g of the magnesium compound (support) prepared in the above (1). The mixture was heated to 40° C. Thereto was added 2.4 mL (23 mmol) of silicon tetrachloride and stirred for 20 minutes, followed by adding 3.4 mL (13 mmol) of di-n-butyl phthalate. The resultant solution was heated to 80° C. and 77 mL (0.70 mol) of titanium tetrachloride was dropwise added using a dropping funnel. Then, the mixture was stirred at an internal temperature of 125° C. for 1 hour to carry out a titanation procedure. After sufficiently washing with dehydrated octane, 122 mL (1.11 mol) of titanium tetrachloride was added and the mixture was stirred at an internal temperature of 125° C. for 2 hours to carry out a second titanation procedure. Sufficient washing with dehydrated octane gave a solid catalyst component.

(3) Propylene Slurry Polymerization

An autoclave made of stainless steel with a stirrer, having an internal volume of 1 L, was fully dried and then subjected to replacement of an atmosphere therein with nitrogen. The autoclave was charged with 500 mL of dehydrated heptane. The autoclave was further charged with 2.0 mmol of triethylaluminum, 0.25 mmol of dicyclopentyldimethoxysilane and 0.0025 mmol, as Ti atom, of the solid catalyst component prepared in the above (2), and hydrogen was introduced up to 0.1 MPa. Then, while propylene was

TABLE 1

| | Item | Unit | Ex. 1 | Ex. 2 | Ex. 3 | Ex. 4 | Com. Ex. 1 | Com. Ex. 2 | Com. Ex. 3 |
|---|---|---|---|---|---|---|---|---|---|
| Support | Sphericity of Metallic Mg (S) | | 1.85 | 1.85 | 1.85 | 2.93 | 5.20 | 5.80 | 6.95 |
| | Initiator | | $I_2$ | $I_2$ | $MgCl_2$ | $I_2$ | $I_2$ | $I_2$ | $MgCl_2$ |
| | Halogen Comp./Mg | (gram atom molar) | 0.019 | 0.0057 | 0.019 | 0.019 | 0.019 | 0.019 | 0.019 |
| | Reaction Temperature | (° C.) | 78 | 50 | 78 | 78 | 78 | 60 | 78 |
| | Number of Rotation | (rpm) | 350 | 525 | 350 | 350 | 350 | 350 | 350 |
| | Average Particle Size ($D_{50}$) | (μm) | 68 | 34 | 69 | 67 | 76 | 62 | 80 |
| | Sphericity (S') | | 1.23 | 1.21 | 1.25 | 1.28 | 1.34 | 1.38 | 1.85 |
| | PDDI (P') | | 3.4 | 3.3 | 3.7 | 3.8 | 4.9 | 3.8 | 6.9 |
| Polymer | Polymerization Activity | (kg/g-Cat) | 16.8 | 24.9 | 16.3 | 15.8 | 13.1 | 15.0 | 12.7 |
| | Stereoregularity ([mmmm]) | (mol %) | 98.3 | 98.4 | 98.2 | 98.3 | 98.2 | 98.3 | 98.3 |
| | Average Particle Size ($D_{50}$) | (μm) | 1230 | 660 | 1210 | 1250 | 1320 | 1040 | 1380 |
| | Sphericity (S") | | 1.23 | 1.20 | 1.24 | 1.29 | 1.36 | 1.40 | 1.90 |
| | PDDI (P") | | 3.5 | 3.4 | 3.8 | 3.8 | 5.2 | 3.9 | 7.2 |

Ex.: Example
Com. Ex.: Comparative Example
Halogen Comp.: Halogen and/or Halogen-containing Compound
PDDI: Particle size Distribution Index Example 5

(1) Preparation of Magnesium Compound

A three-necked flask with a stirrer, having an internal volume of 0.5 L, was replaced with nitrogen gas, and then 122 g (2.64 gram atoms) of dehydrated ethanol, 0.8 g (6.3 mg atoms) of iodine and 8 g (0.33 gram atoms) of metallic magnesium with a particle size distribution index of 1.4 (sieved after cutting and milling) were added therein. The mixture was reacted at 78° C. while stirring (350 rpm) until hydrogen was no longer generated from the system to obtain a magnesium compound (diethoxymagnesium). Table 2 shows the results.

introduced, the autoclave was temperature-increased to 80° C. and pressure-increased to a total pressure of 0.8 MPa, followed by polymerization for 1 hour.

Then, the temperature and the pressure in the autoclave were decreased, and the reaction product was taken out and poured into 2 L of methanol to deactivate the catalyst. The product was separated by filtration and vacuum-dried to give a polypropylene. Table 2 shows the results.

Example 6

(1) Preparation of Magnesium Compound

A magnesium compound was obtained in the same manner as in Example 5(1) except that the amount of iodine was changed to 0.24 g (1.9 mg atoms), the reaction temperature was changed to 50° C. and the number of stirring was changed to 525 rpm. Table 2 shows the results.

(2) Preparation of Solid Catalyst Component

A solid catalyst component was obtained in the same manner as in Example 5(2) except that the magnesium compound prepared in the above (1) was used.

(3) Propylene Slurry Polymerization

Propylene was polymerized in the same manner as in Example 5(3) except that the solid catalyst component prepared in the above (2) was used. Table 2 shows the results.

Example 7

(1) Preparation of Magnesium Compound

A magnesium compound was obtained in the same manner as in Example 5(1) except that the iodine was replaced with 0.30 g of anhydrous magnesium chloride (6.3 mg atoms) in Example 5(1). Table 1 shows the results.

(2) Preparation of Solid Catalyst Component

A solid catalyst component was obtained in the same manner as in Example 5(2) except that the magnesium compound prepared in the above (1) was used.

(3) Propylene Slurry Polymerization

Propylene was polymerized in the same manner as in Example 5(3) except that the solid catalyst component prepared in the above (2) was used. Table 2 shows the results.

Example 8

(1) Preparation of Magnesium Compound

A magnesium compound was obtained in the same manner as in Example 5(1) except that metallic magnesium with a particle size distribution index of 3.0 (sieved after cutting and milling) was used. Table 2 shows the results.

(2) Preparation of Solid Catalyst Component

A solid catalyst component was obtained in the same manner as in Example 5(2) except that the magnesium compound prepared in the above (1) was used.

(3) Propylene Slurry Polymerization

Propylene was polymerized in the same manner as in Example 5(3) except that the solid catalyst component prepared in the above (2) was used. Table 2 shows the results.

Example 9

(1) Preparation of Magnesium Compound

A magnesium compound was obtained in the same manner as in Example 5(1) except that metallic magnesium with a particle size distribution index of 1.8 (sieved after cutting and milling) was used. Table 2 shows the results.

(2) Preparation of Solid Catalyst Component

A solid catalyst component was obtained in the same manner as in Example 5(2) except that the magnesium compound prepared in the above (1) was used.

(3) Propylene Slurry Polymerization

Propylene was polymerized in the same manner as in Example 5(3) except that the solid catalyst component prepared in the above (2) was used. Table 2 shows the results.

Comparative Example 4

(1) Preparation of Magnesium Compound

A magnesium compound was obtained in the same manner as in Example 5(1) except that metallic magnesium with a particle size distribution index of 4.9 (sieved after cutting and milling, and collected particles of widely varied diameters when sieved) was used. Table 2 shows the results.

(2) Preparation of Solid Catalyst Component

A solid catalyst component was obtained in the same manner as in Example 5(2) except that the magnesium compound prepared in the above (1) was used.

(3) Propylene Slurry Polymerization

Propylene was polymerized in the same manner as in Example 5(3) except that the solid catalyst component prepared in the above (2) was used. Table 2 shows the results.

Comparative Example 5

(1) Preparation of Magnesium Compound

A magnesium compound was obtained in the same manner as in Example 5(1) except that metallic magnesium with a particle size distribution index of 5.4 (sieved after cutting and milling, and collected particles of widely varied diameters when sieved) was used and the reaction temperature was changed to 60° C. Table 2 shows the results.

(2) Preparation of Solid Catalyst Component

A solid catalyst component was obtained in the same manner as in Example 5(2) except that the magnesium compound prepared in the above (1) was used (3) Propylene Slurry Polymerization Propylene was polymerized in the same manner as in Example 5(3) except that the solid catalyst component prepared in the above (2) was used. Table 2 shows the results.

Comparative Example 6

(1) Preparation of Magnesium Compound

A magnesium compound was obtained in the same manner as in Example 7(1) except that metallic magnesium with a particle size distribution index of 7.0 (only cut and milled) was used. Table 2 shows the results.

(2) Preparation of Solid Catalyst Component

A solid catalyst component was obtained in the same manner as in Example 5(2) except that the magnesium compound prepared in the above (1) was used.

(3) Propylene Slurry Polymerization

Propylene was polymerized in the same manner as in Example 5(3) except that the solid catalyst component prepared in the above (2) was used. Table 2 shows the results.

TABLE 2

| | Item | Unit | Ex. 5 | Ex. 6 | Ex. 7 | Ex. 8 | Ex. 9 | Com. Ex. 4 | Com. Ex. 5 | Com. Ex. 6 |
|---|---|---|---|---|---|---|---|---|---|---|
| Support | PDDI of Metallic Mg (P) | | 1.4 | 1.4 | 1.4 | 3.0 | 1.8 | 4.9 | 5.4 | 7.0 |
| | Initiator | | $I_2$ | $I_2$ | $MgCl_2$ | $I_2$ | $I_2$ | $I_2$ | $I_2$ | $MgCl_2$ |
| | Halogen Comp./Mg | (gram atom molar) | 0.019 | 0.0057 | 0.019 | 0.019 | 0.019 | 0.019 | 0.019 | 0.019 |

TABLE 2-continued

| | Item | Unit | Ex. 5 | Ex. 6 | Ex. 7 | Ex. 8 | Ex. 9 | Com. Ex. 4 | Com. Ex. 5 | Com. Ex. 6 |
|---|---|---|---|---|---|---|---|---|---|---|
| | Reaction Temperature | (° C.) | 78 | 50 | 78 | 78 | 78 | 78 | 60 | 78 |
| | Number of Rotation | (rpm) | 350 | 525 | 350 | 350 | 350 | 350 | 350 | 350 |
| | Average Particle Size ($D_{50}$) | (μm) | 69 | 34 | 70 | 68 | 69 | 74 | 61 | 77 |
| | PDDI (P') | | 2.8 | 2.6 | 2.9 | 3.1 | 3.2 | 4.8 | 3.8 | 6.2 |
| | Sphericity (S') | | 1.30 | 1.28 | 1.31 | 1.32 | 1.30 | 1.36 | 1.35 | 1.63 |
| Polymer | Polymerization Activity | (kg/g-Cat) | 16.4 | 23.9 | 15.5 | 15.7 | 16.4 | 13.8 | 15.4 | 13.2 |
| | Stereoregularity ([mmmm]) | (mol %) | 98.3 | 98.4 | 98.2 | 98.3 | 98.3 | 98.2 | 98.3 | 98.3 |
| | Average Particle Size ($D_{50}$) | (μm) | 1,240 | 650 | 1,190 | 1,220 | 1,240 | 1,300 | 1,030 | 1,340 |
| | PDDI (P") | | 2.9 | 2.7 | 3.0 | 3.2 | 3.4 | 5.0 | 3.9 | 6.4 |
| | Sphericity (S") | | 1.30 | 1.28 | 1.30 | 1.33 | 1.30 | 1.38 | 1.36 | 1.65 |

Ex.: Example
Com. Ex.: Comparative Example
Halogen Comp.: Halogen and/or Halogen-containing Compound
PDDI: Particle size Distribution Index Example 10

(1) Preparation of Magnesium Compound

A three-necked flask, which has a stirrer with four baffles (maxblend blade, blade diameter (d)=0.09 m) and has an internal volume of 5 L, was replaced with nitrogen gas. The flask was charged with 2,274 g (49 gram atoms) of dehydrated ethanol, 12 g (95 mg atoms) of iodine and 120 g (4.9 gram atoms) of metallic magnesium with an average particle size of 400 μm (cut and milled product) (ethanol/metallic magnesium (ROH/Mg) (molar ratio)=10). The mixture was reacted at 78° C. while stirring (number of stirring (n)=250 (number of revolution per minute) (hereinafter referred to as "rpm"), $n^3d^2=1.27\times10^5$) until hydrogen was no longer generated from the system to obtain a magnesium compound (diethoxymagnesium). Table 3 shows the results.

(2) Preparation of Solid Catalyst Component

A three-necked flask with a stirrer, having an internal volume of 0.5 L, was subjected to replacement of an atmosphere therein with nitrogen gas, and then the flask was charged with 80 mL of dehydrated octane and 16 g of the magnesium compound (support) prepared in the above (1). The mixture was heated to 40° C. Thereto was added 2.4 mL (23 mmol) of silicon tetrachloride and stirred for 20 minutes, followed by adding 3.4 mL (13 mmol) of di-n-butyl phthalate. The resultant solution was heated to 80° C. and 77 mL (0.70 mol) of titanium tetrachloride was dropwise added using a dropping funnel. Then, the mixture was stirred at an internal temperature of 125° C. for 1 hour to carry out a titanation procedure. After sufficiently washing with dehydrated octane, 122 mL (1.11 mol) of titanium tetrachloride was added and the mixture was stirred at an internal temperature of 125° C. for 2 hours to carry out a second titanation procedure. Sufficient washing with dehydrated octane gave a solid catalyst component.

(3) Propylene Slurry Polymerization

An autoclave made of stainless steel with a stirrer, having an internal volume of 1 L, was fully dried and then subjected to replacement of an atmosphere therein with nitrogen. The autoclave was charged with 500 mL of dehydrated heptane. The autoclave was further charged with 2.0 mmol of triethylaluminum, 0.25 mmol of dicyclopentyldimethoxysilane and 0.0025 mmol, as Ti atom, of the solid catalyst component prepared in the above (2), and hydrogen was introduced up to 0.1 MPa. Then, while propylene was introduced, the autoclave was temperature-increased to 80° C. and pressure-increased to a total pressure of 0.8 MPa, followed by polymerization for 1 hour.

Then, the temperature and the pressure in the autoclave were decreased, and the reaction product was taken out and poured into 2 L of methanol to deactivate the catalyst. The product was separated by filtration and vacuum-dried to give a polypropylene. Table 3 shows the results.

Example 11

(1) Preparation of Magnesium Compound

A magnesium compound was obtained in the same manner as in Example 10(1) except that the amount of iodine was changed to 3.6 g (28 mg atoms), the reaction temperature was changed to 50° C. and the number of stirring (n) was changed to 375 rpm ($n^3d^2=4.27\times10^5$). Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Example 12

(1) Preparation of Magnesium Compound

A magnesium compound was obtained in the same manner as in Example 10(1) except that the iodine was replaced with 1.5 g (31 mg atoms) of anhydrous magnesium chloride and 40 g (1.6 g atoms) of metallic magnesium (ROH/Mg=30) was used. Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Example 13

(1) Preparation of Magnesium Compound

A magnesium compound was obtained in the same manner as in Example 10(1) except that metallic magnesium with an average particle size ($D_{50}$) of 75 μm (cut and milled product) was used, ethanol/metallic magnesium (molar ratio) was changed to 8 and the number of stirring (n) was changed to 150 rpm ($n^3d^2=2.73\times10^4$). Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Example 14

(1) Preparation of Magnesium Compound

A magnesium compound was obtained in the same manner as in Example 13(1) except that metallic magnesium with an average particle size ($D_{50}$) of 1,800 μm (cut and milled product) was used and the number of stirring (n) was 400 rpm ($n^3d^2=5.18\times10^5$). Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Comparative Example 7

(1) Preparation of Magnesium Compound

A magnesium compound was obtained in the same manner as in Example 13(1) except that metallic magnesium with an average particle size ($D_{50}$) of 2,400 μm (cutting and milling product) was used and the number of stirring (n) was changed to 250 rpm ($n^3d^2=1.27\times10^5$). Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Comparative Example 8

(1) Preparation of Magnesium Compound

A magnesium compound was obtained in the same manner as in Example 11(1) except that metallic magnesium with an average particle size ($D_{50}$) of 40 μm (cut and milled product) and the amount of iodine was changed to 3.6 g (28 mg atoms) and the number of stirring (n) was changed to 200 rpm ($n^3d^2=6.48\times10^4$). Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Comparative Example 9

(1) Preparation of Magnesium Compound

A magnesium compound was obtained in the same manner as in Example 10(1) except that ethanol/metallic magnesium (molar ratio) was changed to 50. Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Comparative Example 10

(1) Preparation of Magnesium Compound

A magnesium compound was obtained in the same manner as in Example 10(1) except that ethanol/metallic magnesium (molar ratio) was changed to 3. Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Comparative Example 11

(1) Preparation of Magnesium Compound

A magnesium compound was obtained in the same manner as in Example 13(1) except that metallic magnesium with an average particle size ($D_{50}$) of 600 μm (cut and milled product) was used and the number of stirring (n) was changed to 60 rpm ($n^3d^2=1.75\times10^3$). Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

Comparative Example 12

(1) Preparation of Magnesium Compound

A magnesium compound was obtained in the same manner as in Example 13(1) except that metallic magnesium with an average particle size ($D_{50}$) of 200 μm (cut and milled product) was used and the number of stirring (n) was changed to 800 rpm ($n^3d^2=4.15\times10^6$). Table 3 shows the results.

(2) Preparation of Solid Catalyst Component

A solid catalyst component was obtained in the same manner as in Example 10(2) except that the magnesium compound prepared in the above (1) was used.

(3) Propylene Slurry Polymerization

Propylene was polymerized in the same manner as in Example 10(3) except that the solid catalyst component prepared in the above (2) was used. Table 3 shows the results.

TABLE 3

| | Item | Unit | Ex. 10 | Ex. 11 | Ex. 12 | Ex. 13 | Ex. 14 |
|---|---|---|---|---|---|---|---|
| M-Mg Support | Average Particle Size ($D_{50}$) | (μm) | 400 | 400 | 400 | 75 | 1,800 |
| | Initiator | | $I_2$ | $I_2$ | $MgCl_2$ | $I_2$ | $I_2$ |
| | Halogen Comp./Mg | (gram atom molar) | 0.019 | 0.0057 | 0.019 | 0.019 | 0.019 |
| | ROH/Mg | (molar ratio) | 10 | 10 | 30 | 8 | 8 |
| | Reaction temperature | (° C.) | 78 | 50 | 78 | 78 | 78 |
| | Number of Rotation (n) | (rpm) | 250 | 375 | 250 | 150 | 400 |
| | Diameter of Stirring Blade (d) | (m) | 0.09 | 0.09 | 0.09 | 0.09 | 0.09 |
| | Stirring Condition ($n^3d^2$) | | 1.27E+05 | 4.27E+05 | 1.27E+05 | 2.73E+04 | 5.18E+05 |
| | Average Particle Size ($D_{50}$) | (μm) | 72 | 35 | 77 | 34 | 54 |
| | PDDI (P) | | 3.0 | 2.9 | 3.2 | 3.1 | 3.2 |
| | Sphericity (S) | | 1.24 | 1.23 | 1.26 | 1.27 | 1.26 |
| Polymer | Polymerization Activity | (kg/g-Cat) | 15.7 | 23.8 | 14.6 | 16.4 | 16.1 |
| | Stereoregularity ([mmmm]) | (mol %) | 98.4 | 98.4 | 98.3 | 98.3 | 98.4 |
| | Average Particle Size ($D_{50}$) | (μm) | 1,310 | 650 | 1,330 | 580 | 1,040 |
| | PDDI (P') | | 3.1 | 3.0 | 3.3 | 3.2 | 3.3 |
| | Sphericity (S') | | 1.24 | 1.23 | 1.26 | 1.28 | 1.27 |

| | Item | Com. Ex. 7 | Com. Ex. 8 | Com. Ex. 9 | Com. Ex. 10 | Com. Ex. 11 | Com. EX. 12 |
|---|---|---|---|---|---|---|---|
| M-Mg Support | Average Particle Size ($D_{50}$) | 2,400 | 40 | 400 | 400 | 600 | 200 |
| | Initiator | $I_2$ | $I_2$ | $I_2$ | $I_2$ | $I_2$ | $I_2$ |
| | Halogen Comp./Mg | 0.019 | 0.0057 | 0.019 | 0.019 | 0.019 | 0.019 |
| | ROH/Mg | 8 | 10 | 50 | 3 | 8 | 8 |
| | Reaction temperature | 78 | 78 | 78 | 78 | 78 | 78 |
| | Number of Rotation (n) | 250 | 200 | 250 | 250 | 60 | 800 |
| | Diameter of Stirring Blade (d) | 0.09 | 0.09 | 0.09 | 0.09 | 0.09 | 0.09 |
| | Stirring Condition ($n^3d^2$) | 1.27E+05 | 6.48E+04 | 1.27E+05 | 1.27E+05 | 1.75E+03 | 4.15E+06 |
| | Average Particle Size ($D_{50}$) | 103 | 15 | 88 | 64 | 77 | 17 |
| | PDDI (P) | 4.3 | 4.4 | 4.7 | 4.8 | 4.7 | 4.8 |
| | Sphericity (S) | 1.48 | 1.73 | 1.63 | 1.65 | 1.98 | 1.78 |
| Polymer | Polymerization Activity | 13.2 | 12.9 | 12.7 | 11.9 | 12.5 | 12.2 |
| | Stereoregularity ([mmmm]) | 98.1 | 98.2 | 98.3 | 98.2 | 98.2 | 98.3 |
| | Average Particle Size ($D_{50}$) | 1,800 | 330 | 1,690 | 1,220 | 1,340 | 360 |
| | PDDI (P') | 4.5 | 4.8 | 4.9 | 5.0 | 4.9 | 5.1 |
| | Sphericity (S') | 1.48 | 1.75 | 1.65 | 1.68 | 2.04 | 1.48 |

Ex.: Example
Com. Ex.: Comparative Example
M-Mg: Metallic Mg
Halogen Comp.: Halogen and/or Halogen-containing Compound
PDDI: Particle size Distribution Index

Example 15

(1) Preparation of Magnesium Compound

A three-necked flask with a stirrer, having an internal volume of 0.5 L, was replaced with nitrogen gas. The flask was charged with 122 g (2.64 gram atoms) of dehydrated ethanol, 0.8 g (6.3 mg atoms) of iodine and 8 g (0.33 gram atoms) of metallic magnesium with an oxidized coating film having a thickness of 0.05 μm (an average particle size of 400 μm, obtained by cut, milled and sieved under an atmosphere of nitrogen gas). The mixture was reacted at 78° C. while stirring (number of stirring (n)=350 rpm) until hydrogen was no longer generated from the system to obtain a magnesium compound (diethoxymagnesium). Table 4 shows the results.

(2) Preparation of Solid Catalyst Component

A three-necked flask with a stirrer, having an internal volume of 0.5 L, was subjected to replacement of an atmosphere therein with nitrogen gas, and then the flask was charged with 80 mL of dehydrated octane and 16 g of the magnesium compound (support) prepared in the above (1). The mixture was heated to 40° C. Thereto was added 2.4 mL (23 mmol) of silicon tetrachloride and stirred for 20 minutes, followed by adding 3.4 mL (13 mmol) of di-n-butyl phthalate. The resultant solution was heated to 80° C. and 77 mL (0.70 mol) of titanium tetrachloride was dropwise added using a dropping funnel. Then, the mixture was stirred at an internal temperature of 125° C. for 1 hour to carry out a titanation procedure. After sufficiently washing with dehydrated octane, 122 mL (1.11 mol) of titanium tetrachloride was added and the mixture was stirred at an internal temperature of 125° C. for 2 hours to carry out a second titanation procedure. Sufficient washing with dehydrated octane gave a solid catalyst component.

(3) Propylene Slurry Polymerization

An autoclave made of stainless steel with a stirrer, having an internal volume of 1 L, was fully dried and then subjected to replacement of an atmosphere therein with nitrogen. The autoclave was charged with 500 mL of dehydrated heptane. The autoclave was further charged with 2.0 mmol of triethylaluminum, 0.25 mmol of dicyclopentyldimethoxysilane and 0.0025 mmol, as Ti atom, of the solid catalyst component prepared in the above (2), and hydrogen was introduced up to 0.1 MPa. Then, while propylene was introduced, the autoclave was temperature-increased to 80° C. and pressure-increased to a total pressure of 0.8 MPa, followed by polymerization for 1 hour.

Then, the temperature and the pressure in the autoclave were decreased, and the reaction product was taken out and poured into 2 L of methanol to deactivate the catalyst. The product was separated by filtration and vacuum-dried to give a polypropylene. Table 4 shows the results.

Example 16

(1) Preparation of Magnesium Compound

A magnesium compound was obtained in the same manner as in Example 15(1) except that the amount of iodine was changed to 0.24 g (1.9 mg atoms), the reaction temperature was changed to 50° C. and the number of stirring was changed to 525 rpm. Table 4 shows the results.

(2) Preparation of Solid Catalyst Component

A solid catalyst component was obtained in the same manner as in Example 15(2) except that the magnesium compound prepared in the above (1) was used.

(3) Propylene Slurry Polymerization

Propylene was polymerized in the same manner as in Example 15(3) except that the solid catalyst component prepared in the above (2) was used. Table 4 shows the results.

Example 17

(1) Preparation of Magnesium Compound

A magnesium compound was obtained in the same manner as in Example 15(1) except that the iodine was replaced with 0.30 g (6.3 mg atoms) of anhydrous magnesium chloride in Example 15(1). Table 4 shows the results.

(2) Preparation of Solid Catalyst Component

A solid catalyst component was obtained in the same manner as in Example 15(2) except that the magnesium compound prepared in the above (1) was used.

(3) Propylene Slurry Polymerization

Propylene was polymerized in the same manner as in Example 15(3) except that the solid catalyst component prepared in the above (2) was used. Table 3 shows the results.

Example 18

(1) Preparation of Magnesium Compound

A magnesium compound was obtained in the same manner as in Example 15(1) except that metallic magnesium having an oxidized coating film with a thickness of 0.5 μm (an average particle size of 400 μm, obtained by cut, milled and sieved under an atmosphere of nitrogen gas) was used. Table 4 shows the results.

(2) Preparation of Solid Catalyst Component

A solid catalyst component was obtained in the same manner as in Example 15(2) except that the magnesium compound prepared in the above (1) was used.

(3) Propylene Slurry Polymerization

Propylene was polymerized in the same manner as in Example 15(3) except that the solid catalyst component prepared in the above (2) was used. Table 4 shows the results.

Comparative Example 13

(1) Preparation of Magnesium Compound

A magnesium compound was obtained in the same manner as in Example 15(1) except that metallic magnesium having an oxidized coating film with a thickness of 2 μm (an average particle size of 300 μm, obtained by cut, milled and sieved in air) was used. Table 4 shows the results.

(2) Preparation of Solid Catalyst Component

A solid catalyst component was obtained in the same manner as in Example 15(2) except that the magnesium compound prepared in the above (1) was used.

(3) Propylene Slurry Polymerization

Propylene was polymerized in the same manner as in Example 15(3) except that the solid catalyst component prepared in the above (2) was used. Table 4 shows the results.

Comparative Example 14

(1) Preparation of Magnesium Compound

A magnesium compound was obtained in the same manner as in Example 17(1) except that the same metallic magnesium as that in Comparative Example 1 was used. Table 4 shows the results.

(2) Preparation of Solid Catalyst Component

A solid catalyst component was obtained in the same manner as in Example 15(2) except that the magnesium compound prepared in the above (1) was used.

(3) Propylene Slurry Polymerization

Propylene was polymerized in the same manner as in Example 15(3) except that the solid catalyst component prepared in the above (2) was used. Table 4 shows the results.

Comparative Example 15

(1) Preparation of Magnesium Compound

A magnesium compound was obtained in the same manner as in Example 15(1) except that the same metallic magnesium as that in Comparative Example 13 was used and the reaction temperature was changed to 60° C. Table 4 shows the results.

(2) Preparation of Solid Catalyst Component

A solid catalyst component was obtained in the same manner as in Example 15(2) except that the magnesium compound prepared in the above (1) was used.

(3) Propylene Slurry Polymerization

Propylene was polymerized in the same manner as in Example 15(3) except that the solid catalyst component prepared in the above (2) was used. Table 4 shows the results.

without reducing stereoregularity and catalyst properties such as polymerization activity by using the magnesium compound of the invention.

The invention claimed is:

1. A method for producing a magnesium compound, comprising reacting metallic magnesium having a sphericity (S) of less than 2.50, the sphericity (S) being represented by the following formula (I), an alcohol, and a halogen and/or a halogen-containing compound containing halogen atoms in an amount of 0.0001 gram atom or more relative to one gram atom of the metallic magnesium, $$S=(L_1/L_2)^3 \quad (I)$$

wherein $L_1$ represents a maximum diameter of projection views of metallic magnesium determined by imaging metallic magnesium with a scanning electron microscope, and $L_2$ represents the diameter of a circle having an area equal to the area of the projection view of metallic magnesium having said maximum diameter $L_1$;

wherein the magnesium compound has a sphericity (S') of less than 1.30, the sphericity (S') being represented by the following formula (III), $$S'=(L_3/L_4)^3 \quad (III)$$

wherein $L_3$ represents a maximum diameter of projection views of the magnesium compound determined by

TABLE 4

| | Item | Unit | Ex. 15 | Ex. 16 | Ex. 17 | Ex. 18 | Com. Ex. 13 | Com. Ex. 14 | Com. Ex. 15 |
|---|---|---|---|---|---|---|---|---|---|
| Support | Thickness of Oxidized Film of Metallic Mg | (μm) | 0.05 | 0.05 | 0.05 | 0.5 | 2 | 2 | 2 |
| | Initiator | | $I_2$ | $I_2$ | $MgCl_2$ | $I_2$ | $I_2$ | $MgCl_2$ | $I_2$ |
| | Halogen Comp./Mg | (gram atom molar) | 0.019 | 0.0057 | 0.019 | 0.019 | 0.019 | 0.019 | 0.019 |
| | Reaction Temperature | (° C.) | 78 | 50 | 78 | 78 | 78 | 78 | 60 |
| | Number of Rotation | (rpm) | 350 | 525 | 350 | 350 | 350 | 350 | 350 |
| | Average Particle Size ($D_{50}$) | (μm) | 68 | 35 | 69 | 70 | 72 | 73 | 49 |
| | PDDI (P) | | 3.0 | 2.9 | 3.0 | 3.2 | 4.7 | 4.9 | 3.8 |
| | Sphericity (S) | | 1.30 | 1.28 | 1.32 | 1.31 | 1.50 | 1.53 | 1.40 |
| Polymer | Polymerization Activity | (kg/g-Cat) | 16.2 | 24.2 | 15.9 | 15.0 | 13.3 | 13.2 | 14.9 |
| | Stereoregularity ([mmmm]) | (mol %) | 98.4 | 98.4 | 98.3 | 98.3 | 98.2 | 98.2 | 98.3 |
| | Average Particle Size ($D_{50}$) | (μm) | 1,250 | 650 | 1,200 | 1,220 | 1,250 | 1,280 | 1,080 |
| | PDDI (P') | | 3.1 | 2.9 | 3.1 | 3.3 | 4.6 | 4.8 | 3.942 |
| | Sphericity (S') | | 1.29 | 1.28 | 1.32 | 1.31 | 1.52 | 1.55 | 1.64 |

Ex.: Example
Com. Ex.: Comparative Example
Halogen Comp.: Halogen and/or Halogen-containing Compound
PDDI: Particle size Distribution Index

INDUSTRIAL UTILITY

The invention can provide a magnesium compound, a solid catalyst component for olefin polymerization, a catalyst for olefin polymerization and a method for producing a polyolefin. A polyolefin with a narrow particle size distribution and/or a nearly spherical form can be obtained imaging the magnesium compound with a scanning electron microscope, and $L_4$ represents the diameter of a circle having an area equal to the area of the projection view of the magnesium compound having said maximum diameter $L_3$.

2. The method according to claim 1, wherein the halogen is iodine.

3. The method according to claim 1, wherein the halogen-containing compound is magnesium chloride.

4. The method according to claim 1, wherein the metallic magnesium, the alcohol and the halogen and/or the halogen-containing compound are reacted at a temperature of from 30 to 90° C.

* * * * *

UNITED STATES PATENT AND TRADEMARK OFFICE
CERTIFICATE OF CORRECTION

PATENT NO.       : 7,387,979 B2  
APPLICATION NO.  : 10/515766  
DATED            : June 17, 2008  
INVENTOR(S)      : Shojiro Tanase et al.

Page 1 of 1

It is certified that error appears in the above-identified patent and that said Letters Patent is hereby corrected as shown below:

On the Title Page  
(75) Inventors

Correct the spelling of the last-listed inventor to:     Masahiko KURAMOTO

Signed and Sealed this

Twenty-fifth Day of November, 2008

JON W. DUDAS  
*Director of the United States Patent and Trademark Office*